(12) United States Patent
Olde et al.

(10) Patent No.: US 9,632,018 B2
(45) Date of Patent: Apr. 25, 2017

(54) METHOD AND DEVICE FOR MONITORING THE INTEGRITY OF A CONNECTION SYSTEM

(75) Inventors: Bo Olde, Lund (SE); Kristian Solem, Kavlinge (SE)

(73) Assignee: Gambro Lundia AB, Lund (SE)

( * ) Notice: Subject to any disclaimer, the term of this patent is extended or adjusted under 35 U.S.C. 154(b) by 1216 days.

(21) Appl. No.: 13/519,245

(22) PCT Filed: Dec. 22, 2010

(86) PCT No.: PCT/EP2010/070560
§ 371 (c)(1),
(2), (4) Date: Aug. 30, 2012

(87) PCT Pub. No.: WO2011/080193
PCT Pub. Date: Jul. 7, 2011

(65) Prior Publication Data
US 2013/0204542 A1    Aug. 8, 2013

Related U.S. Application Data

(60) Provisional application No. 61/290,313, filed on Dec. 28, 2009.

(30) Foreign Application Priority Data

Dec. 28, 2009    (SE) ...................................... 0951026

(51) Int. Cl.
*B01D 61/32*    (2006.01)
*G01N 19/08*    (2006.01)
(Continued)

(52) U.S. Cl.
CPC ........... *G01N 19/08* (2013.01); *A61M 1/3653* (2013.01); *A61M 1/3656* (2014.02); *A61B 5/024* (2013.01);
(Continued)

(58) Field of Classification Search
CPC ........... G01M 3/00; G01M 3/243; A61M 1/36
(Continued)

(56) References Cited

U.S. PATENT DOCUMENTS

| | | | |
|---|---|---|---|
| 6,077,443 | A | 6/2000 | Goldau |
| 6,623,443 | B1 | 9/2003 | Polaschegg |

(Continued)

FOREIGN PATENT DOCUMENTS

| | | |
|---|---|---|
| DE | 197 34 002 | 9/1998 |
| DE | 199 01 078 | 2/2000 |

(Continued)

*Primary Examiner* — Lam Nguyen
(74) *Attorney, Agent, or Firm* — Mueting, Raasch & Gebhardt, P.A.

(57) ABSTRACT

A device is configured to monitor the integrity of a connection system between first and second fluid containing systems comprising first and second pulse generators. A pressure sensor is arranged in the first fluid containing system to detect first pulses originating from the first pulse generator and second pulses originating from the second pulse generator. The device operates a monitoring method, by generating (42) a time-dependent pressure signal based on measurement data obtained from the pressure sensor such that the pressure signal contains a sequence of apparent pulses. The apparent pulses represent a superposition of the second pulses on the first pulses when the connection system (C) is intact. The device processes (44) the pressure signal to calculate a parameter value based on a pulse feature of at least one of the apparent pulses in the pressure signal. The parameter value represents a disturbance caused by the superposition of the second pulses on the first pulses, and may be given as a measure of statistical dispersion, pulse-to-pulse symmetry, or first pulse similarity. The device determines (45) the integrity of the connection system based at least partly on the parameter value. The first fluid con- (Continued)

taining system may be an extracorporeal blood circuit, and the second fluid containing system may be a human or animal subject.

28 Claims, 13 Drawing Sheets

(51) Int. Cl.
*A61B 5/024* (2006.01)
*A61M 1/36* (2006.01)
*A61M 5/168* (2006.01)

(52) U.S. Cl.
CPC . *A61B 2562/0247* (2013.01); *A61B 2562/226* (2013.01); *A61M 1/3639* (2013.01); *A61M 5/16859* (2013.01); *A61M 2205/13* (2013.01); *A61M 2205/15* (2013.01); *A61M 2205/3331* (2013.01); *A61M 2230/04* (2013.01); *A61M 2230/06* (2013.01)

(58) Field of Classification Search
USPC .............................. 210/646, 741; 604/6.11
See application file for complete search history.

(56) References Cited

U.S. PATENT DOCUMENTS

| | | |
|---|---|---|
| 2005/0010118 A1 | 1/2005 | Toyoda |
| 2010/0234787 A1 | 9/2010 | Masaoka |

FOREIGN PATENT DOCUMENTS

| | | |
|---|---|---|
| EP | 0 328 162 | 8/1989 |
| WO | WO 97/10013 | 3/1997 |
| WO | WO 2009/038834 | 3/2009 |
| WO | WO 2009/060741 | 5/2009 |
| WO | WO 2009/127683 | 10/2009 |
| WO | WO 2009/031560 | 12/2009 |
| WO | WO 2009/156174 | 12/2009 |

METHOD AND DEVICE FOR MONITORING THE INTEGRITY OF A CONNECTION SYSTEM

This application is a U.S. National Stage Application of International Application No. PCT/EP2010/070560, filed Dec. 22, 2010, which was published in English on Jul. 7, 2011 as International Patent Publication WO 2011/080193 A1, and which claims the benefit under 35 U.S.C. 119(e) of U.S. Provisional Application No. 61/290,313 filed Dec. 28, 2009. International Application No. PCT/EP2010/070560 also claims priority to Swedish Application No. 0951026-4 filed Dec. 28, 2009.

TECHNICAL FIELD

The present invention generally relates to monitoring of fluid connections, and in particular to monitoring the integrity of a connection system based on a pressure measurement. The present invention is e.g. applicable in arrangements for extracorporeal blood treatment.

BACKGROUND ART

In extracorporeal blood treatment, blood is taken out of a patient, treated and then reintroduced into the patient by means of an extracorporeal blood flow circuit. Generally, the blood is circulated through the circuit by one or more pumping devices. The circuit is connected to a blood vessel access of the patient, typically via one or more access devices, such as needles or catheters, which are inserted into a blood vessel access. Such extracorporeal blood treatments include hemodialysis, hemodiafiltration, hemofiltration, plasmapheresis, blood fraction separation (e.g. cells) of donor blood, etc.

In extracorporeal blood treatment, it is vital to minimize the risk for malfunctions in the extracorporeal blood flow circuit, since these may lead to a potentially life-threatening condition of the patient. Serious conditions may arise if the extracorporeal blood flow circuit is disrupted, e.g. by an access device for blood extraction (e.g. an arterial needle/catheter) coming loose from the blood vessel access, causing air to be sucked into the circuit which leads to air embolism in the patient and increased risk of clotting in the circuit, or by an access device for blood reintroduction (e.g. a venous needle/catheter) coming loose from the blood vessel access, causing the patient to be drained of blood within minutes. Other malfunctions may be caused by the blood vessel access becoming blocked or obstructed, or by the access device being positioned too close to the walls of the blood vessel access, or by constriction/occlusion of the access device due to clotting.

These malfunctions all originate in a "connection system" between the patient and the extracorporeal blood flow circuit. The connection system includes one or more access devices and possibly one or more releasable connectors for attaching the access devices to tubing in the extracorporeal blood flow circuit.

An apparatus for extracorporeal blood treatment may include one or more surveillance devices that monitor the integrity of the blood flow circuit and issue an alarm and/or cause appropriate action to be taken whenever a potentially dangerous situation is detected. Such surveillance devices may operate on measurement signals from one or more pressure sensors in the circuit. Conventionally, the monitoring during a blood treatment is carried out by comparing one or more measured average pressure levels with one or more threshold values and/or by monitoring the presence of air bubbles using an air detector in the circuit. For example, failure in the blood extraction may involve air being introduced into the circuit, whereby the measured average pressure may approach atmospheric pressure, or the blood flow being blocked or obstructed, whereby the measured average pressure may drop to a low level. A failure in the reintroduction of blood into the blood vessel access due to a failure in the connection system may be detectable as a decrease in the measured average pressure. However, it may be difficult to set appropriate threshold values, since the average pressure in the circuit may vary between treatments, and also during a treatment, e.g. as a result of the patient moving. Further, if an access device comes loose and gets stuck in bed sheets or the patient's clothes, the measured average pressure might not change enough to indicate the potentially dangerous situation.

To increase the monitoring precision, WO 97/10013 proposes detecting, as one of several options, a heart signal in the measured pressure and using the heart signal as an indicator of the integrity of a fluid connection between an extracorporeal blood flow circuit and a blood vessel access. The heart signal represents a pressure wave which is produced by the patient's heart and transmitted from the patient's circulatory system to the extracorporeal blood flow circuit via the blood vessel access. Malfunctions in the fluid connection will disturb the transmission of the heart-generated pressure wave to the circuit, causing the heart signal to change or even disappear. The measured pressure may also include a strong pressure wave produced by the blood pump in the extracorporeal blood flow circuit. In WO 97/10013, the monitoring involves filtering a measured pressure signal to remove the frequency components that originate from the blood pump, and then detecting the heart signal by analysing the filtered pressure signal. The amplitude of the filtered pressure signal is then taken as an indication of the integrity of the fluid connection.

US2005/0010118 proposes a solution which involves applying a frequency analysis to a measured pressure signal to generate a frequency spectrum, and monitoring anomalies of the fluid connection based on the intensity of the frequency component caused by the patient's heartbeat. US2005/0010118 proposes various solutions on how to identify only the frequency component caused by the patient's heartbeat in the frequency spectrum, which consists of a mixture of various frequency components, including those caused by pumps in the extracorporeal blood flow circuit. The proposed solutions all involve a subtraction of a reference frequency spectrum from the frequency spectrum obtained from the pressure signal. The reference frequency spectrum may be obtained from the pressure signal prior to installation of the fluid connection, may be synthesized based on the operating frequency of the pumps, or may be obtained from the pressure signal at a earlier point in time. Irrespective of solution, the result of the subtraction is processed for extraction of a parameter value that represents the intensity of the frequency component caused by the patient's heartbeat. If the parameter value falls below an threshold value, an anomaly of the fluid connection is deemed to have occurred.

All of the above techniques may require significant processing of the pressure signal for removal of pump signals originating from pumping devices in the extracorporeal circuit, and for calculation of a parameter value that properly represents the remaining heart signal. If the filtering fails, so that a portion of the pump signals remains in the signal to be analysed, the parameter value may erroneously indicate presence of a heart signal even if the integrity of the fluid connection is in fact compromised.

The prior art also comprises WO2009/127683, which discloses a technique for monitoring the integrity of an the extracorporeal blood flow circuit in fluid communication with a blood vessel of a patient, by isolating a beating signal in a pressure signal obtained from a pressure sensor in the extracorporeal blood flow circuit. The beating signal manifests itself as a slow amplitude modulation of the pressure signal and is formed by interference between pressure waves generated by the patient's heart and pressure waves generated by a pumping device in the extracorporeal blood flow circuit. Absence of the beating signal is taken as an indication that the integrity of the circuit is compromised. This technique is suited for detection of a heart signal that lies close in frequency to the pump signal, and typically involves filtering of the pressure signal in a narrow passband around a specific frequency component of the pump signal, where the resulting parameter value is calculated to indicate presence or absence of the slowly varying amplitude in the filtered pressure signal.

Corresponding needs to monitor the integrity of a connection system between first and second fluid containing systems may arise in other fields of technology.

SUMMARY

It is an object of the invention to at least partly overcome one or more limitations of the prior art. Specifically, it is an object to provide an alternative or complementary technique for monitoring the integrity of a connection system between first and second fluid containing systems using a pressure measurement, e.g. with a reduced need for processing and/or an increased versatility and/or an improved robustness and/or an increased certainty of detecting a malfunction in the connection system.

This and other objects, which will appear from the description below, are at least partly achieved by means of a method, devices, and a computer program product according to the independent claims, embodiments thereof being defined by the dependent claims.

Different aspects and embodiments of the invention are based on the ground-breaking insight that the processing for isolation of the heart signal or a beating signal may be dispensed with, and that the integrity of the connection system may be monitored by analysing apparent pulses that are formed in the time domain by the combination of the heart signal and the pump signal. Thus, the integrity is determined based on a parameter value, which is calculated to represent the disturbance caused by the superposition of the heart pulses on the pump pulses. A "superposition" of pulses is intended to mean that different pulses in the pressure signal are added together. This is not to be confused with the superposition of pressure waves that give rise to a beating signal, which thus is distinct from a disturbance caused by superposition of pulses in a pressure signal.

As noted above, the underlying problems, and thus also the inventive solution, are generally applicable for monitoring the integrity of a connection system between first and second fluid containing systems.

Accordingly, a first aspect of the invention is a method for monitoring the integrity of a connection system between first and second fluid containing systems, wherein the first fluid containing system comprises a first pulse generator, and the second fluid containing system comprises a second pulse generator, and wherein at least one pressure sensor is arranged in the first fluid containing system to detect first pulses originating from the first pulse generator and second pulses originating from the second pulse generator, said method comprising: generating a time-dependent monitoring signal based on measurement data obtained from said at least one pressure sensor such that the monitoring signal contains a sequence of apparent pulses, said apparent pulses representing a superposition of the second pulses on the first pulses when the connection system is intact; processing the monitoring signal to calculate a parameter value based on a pulse feature of at least one of the apparent pulses in the monitoring signal, the parameter value representing a disturbance caused by the superposition of the second pulses on the first pulses; and determining the integrity of the connection system based at least partly on the parameter value.

A second aspect of the invention is a computer program product comprising instructions for causing a computer to perform the method according to the first aspect.

A third aspect of the invention is a device for monitoring the integrity of a connection system between first and second fluid containing systems, wherein the first fluid containing system comprises a first pulse generator, and the second fluid containing system comprises a second pulse generator, and wherein at least one pressure sensor is arranged in the first fluid containing system to detect first pulses originating from the first pulse generator and second pulses originating from the second pulse generator, said device comprising: means for generating a time-dependent monitoring signal based on measurement data obtained from said at least one pressure sensor such that the monitoring signal contains a sequence of apparent pulses, said apparent pulses representing a superposition of the second pulses on the first pulses when the connection system is intact; means for processing the monitoring signal to calculate a parameter value based on pulse feature of at least one of the apparent pulses in the monitoring signal, the parameter value representing a disturbance caused by the superposition of the second pulses on the first pulses; and means for determining the integrity of the connection system based at least partly on the parameter value.

A fourth aspect of the invention is a device for monitoring the integrity of a connection system between first and second fluid containing systems, wherein the first fluid containing system comprises a first pulse generator, and the second fluid containing system comprises a second pulse generator, and wherein at least one pressure sensor is arranged in the first fluid containing system to detect first pulses originating from the first pulse generator and second pulses originating from the second pulse generator, said device comprising: an input for obtaining measurement data from said at least one pressure sensor, and a signal processor connected to said input and being configured to generate a time-dependent monitoring signal based on the measurement data, such that the monitoring signal contains a sequence of apparent pulses, said apparent pulses representing a superposition of the second pulses on the first pulses when the connection system (C) is intact; to process the monitoring signal for calculation of a parameter value based on a pulse feature of at least one of the apparent pulses in the monitoring signal, the parameter value representing a disturbance caused by the superposition of the second pulses on the first pulses; and to determine the integrity of the connection system based at least partly on the parameter value.

Still other objectives, features, aspects and advantages of the present invention will appear from the following detailed description, from the attached claims as well as from the drawings.

BRIEF DESCRIPTION OF THE DRAWINGS

Embodiments of the inventive concepts will now be described in more detail with reference to the accompanying schematic drawings.

DETAILED DESCRIPTION OF EXEMPLARY EMBODIMENTS

Figure 1:
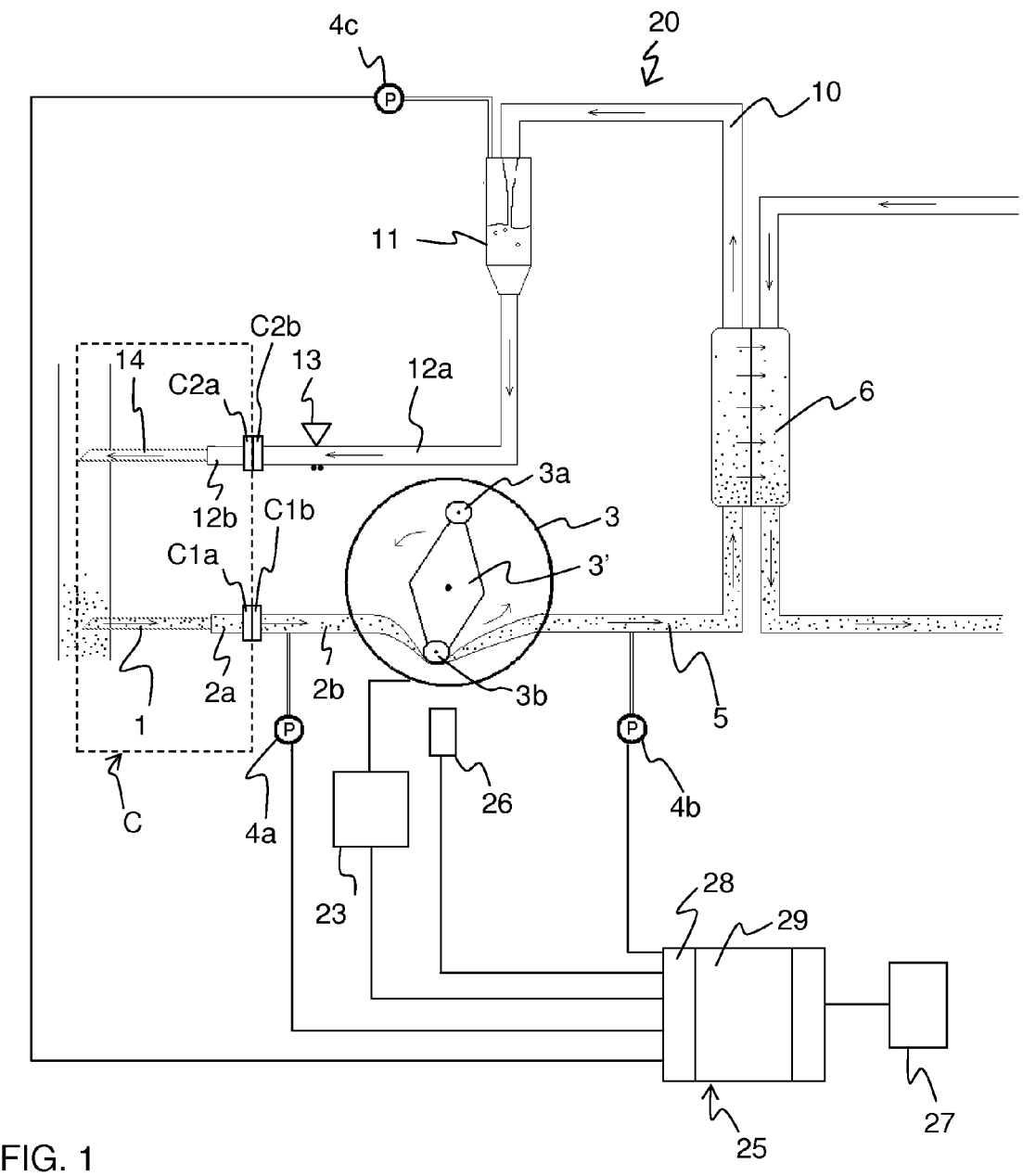
FIG. 1 is a schematic view of a system for hemodialysis treatment including an extracorporeal blood flow circuit.

In the following, different embodiments for monitoring the integrity of a connection system will be described with reference to an extracorporeal blood flow circuit included in a dialysis machine. It is to be understood that corresponding embodiments may be implemented in other types of fluid containing systems, as exemplified at the end of the description.

Throughout the following description, like elements are designated by the same reference numerals.

I. Example of Extracorporeal Circuit

FIG. 1 shows an example of an extracorporeal blood flow circuit 20 of the type which is used for dialysis. The extracorporeal blood flow circuit 20 is connected to the vascular system of a patient by means of a connection system C. The connection system C comprises an arterial access device 1 for blood extraction (here in the form of an arterial needle), a connection tube segment 2a and a connector C1a. The connection system C also comprises a venous access device 14 for blood reintroduction (here in the form of a venous needle), a connection tube segment 12b, and a connector C2a. The connectors C1a, C2a are arranged to provide a releasable or permanent engagement with a corresponding connector C1b, C2b in the circuit 20 so as to form a blood path between the circuit 20 and the arterial needle 1 and the venous needle 14, respectively. The connectors C1a, C1b, C2a, C2b may be of any known type.

In the illustrated example, the extracorporeal circuit 20 comprises the connector C1b, an arterial tube segment 2b, and a blood pump 3 which may be of peristaltic type, as indicated in FIG. 1. At the inlet of the pump there is a pressure sensor 4a (hereafter referred to as "arterial sensor") which measures the pressure before the pump in the arterial tube segment 2b. The blood pump 3 forces the blood, via a tube segment 5, to the blood-side of a dialyser 6. Many dialysis machines are additionally provided with a pressure sensor 4b that measures the pressure between the blood pump 3 and the dialyser 6. The blood is led via a tube segment 10 from the blood-side of the dialyser 6 to a venous drip chamber or deaeration chamber 11 and from there back to the connection system C via a venous tube segment 12a and the connector C2b. A pressure sensor 4c (hereafter referred to as "venous sensor") is provided to measure the pressure on the venous side of the dialyser 6. In the illustrated example, the venous sensor 4c measures the pressure in the venous drip chamber 11. Both the arterial needle 1 and the venous needle 14 are connected to the vascular system of a human or animal patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters.

Herein, the "venous side" of the extracorporeal circuit 20 refers to the part of the blood path located downstream of the blood pump 3, whereas the "arterial side" of the extracorporeal circuit 20 refers to the part of the blood path located upstream of the blood pump 3. In the example of FIG. 1, the venous side is made up of tube segment 5, the blood-side of the dialyser 6, tube segment 10, drip chamber 11 and tube segment 12a, and the arterial side is made up of tube segment 2b.

In FIG. 1, a control unit 23 is provided, inter alia, to control the blood flow in the circuit 20 by controlling the revolution speed of the blood pump 3. The extracorporeal blood flow circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

Further, in FIG. 1, a surveillance/monitoring device 25 is configured to monitor proper operation of the circuit 20, specifically by processing a measurement signal obtained from one or more of the pressure sensors 4a-4c. The detection of a fault condition may bring the device 25 to activate an alarm and/or stop the blood flow, e.g. by stopping the blood pump 3 and activating one or more clamping devices 13 (only one shown) on the tube segments 2a, 2b, 5, 10, 12a, 12b.

As indicated in FIG. 1, the device 25 may also be connected to the control unit 23. Alternatively or additionally, the device 25 may be connected to a pump sensor 26, such as a rotary encoder (e.g. conductive, optical or magnetic) or the like, for indicating the frequency and phase of the blood pump 3. In another variant, the pump sensor 26 may be arranged to sense the frequency and phase based on the current or power fed to the motor driving the blood pump 3. The device 25 is tethered or wirelessly connected to a local or remote device 27 for generating an audible/visual/tactile alarm or warning signal. The surveillance device 25 and/or the alarm device 27 may alternatively be incorporated as part of a dialysis apparatus.

In the various embodiments described herein, pulse generators in the patient and the extracorporeal blood flow circuit generate pressure waves which propagate in the liquid system extending from the respective pulse generator to a pressure sensor, which is in direct or indirect hydrostatic contact with the liquid system. A "pressure wave" is a mechanical wave in the form of a disturbance that travels or propagates through a material or substance. The pressure waves typically propagate in the liquid system at a velocity of about 3-20 m/s. The pressure sensor generates measurement data that forms a pressure pulse for each pressure wave. A "pressure pulse" or "pulse" is thus a set of data samples that define a local increase or decrease (depending on implementation) in signal magnitude within a time-dependent pressure signal. The pressure pulses appear at a rate proportional to the generation rate of the pressure waves at the pulse generator. The pressure sensor may be of any type, e.g. operating by resistive, capacitive, inductive, magnetic or optical sensing, and using one or more diaphragms, bellows, Bourdon tubes, piezo-electrical components, semiconductor components, strain gauges, resonant wires, photoplethysmography (PPG), accelerometers, bioimpedance, etc.

In FIG. 1, the surveillance device 25 comprises a data acquisition part 28 for sampling the measurement data from the pressure sensor(s) 4a-4c and, optionally, for pre-processing the pressure signal that is formed by the sampled measurement data. For example the data acquisition part 28 may include an A/D converter with a required minimum sampling rate and resolution, one or more signal amplifiers, one or more filters to remove undesired signal components in the measurement data, such as offset, high frequency noise and supply voltage disturbances. Generally, the measurement data is acquired as a time sequence of data samples, each representing an instantaneous pressure of the blood in the circuit at the location of the relevant pressure sensor 4a-4c. The pre-processing in the data acquisition part 28 results in a pre-processed pressure signal, which is provided as input to a data analysis part 29 that executes the actual monitoring process. As used herein, the pressure signal, possibly pre-processed, is also denoted a "monitoring signal".

Depending on implementation, the surveillance device 25 may use digital components or analog components, or a combination thereof, for generating, processing and analysing the monitoring signal.

FIG. 2(a) shows an example of a pressure signal (monitoring signal) in the time domain, and FIG. 2(b) shows the corresponding energy spectral density, i.e. signal amplitude as a function of frequency. The energy spectral density reveals that the pressure signal contains a number of different frequency components emanating from the blood pump 3. In the illustrated example, there is a frequency component at the base frequency ($f_0$) of the blood pump (at 1.5 Hz in this example), as well as its harmonics 2 $f_0$, 3 $f_0$ and 4 $f_0$. The base frequency, also denoted pumping frequency in the following, is the frequency of the pump strokes that generate pressure waves in the extracorporeal blood flow circuit. For example, in a peristaltic pump of the type shown in FIG. 1, two pump strokes are generated for each full revolution of the rotor 3', i.e. one pump stroke for each roller 3a, 3b. Thus, each revolution results in two pressure pulses which often dominate in the pressure signal. The exemplifying energy spectrum in FIG. 2(b) indicates the further presence of a frequency component at half the pumping frequency (0.5 $f_0$) and harmonics thereof, in this example at least $f_0$, 1.5 $f_0$, 2 $f_0$ and 2.5 $f_0$. FIG. 2(b) also shows a heart signal (at 1.1 Hz) which in this example is approximately 40 times weaker than the blood pump signal at the base frequency $f_0$.

Figure 2:
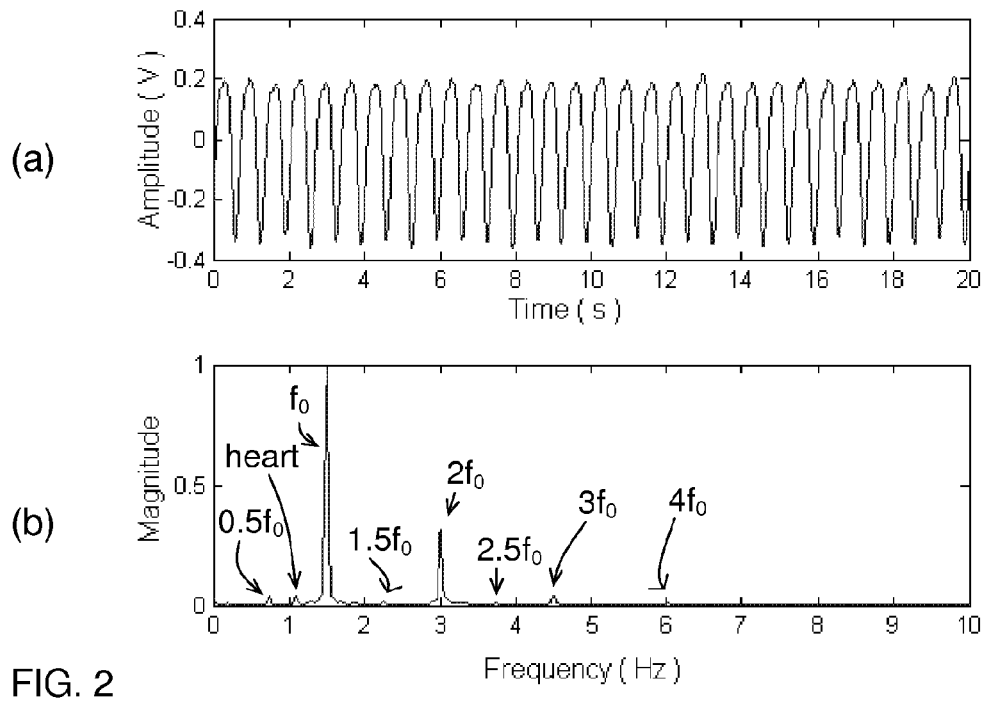
FIG. 2(a) is a plot in the time domain of a pressure signal containing both pump frequency components and a heart signal.
FIG. 2(b) is a plot of the corresponding signal in the frequency domain.

Although not shown in FIG. 2, the pressure signal may also contain repetitive pressure pulses originating from other mechanical pulse generators (not shown) in the circuit 20, such as valves, a pump for dialysis fluid, etc. Repetitive pressure pulses may also originate from mechanical resonance of system components such as swinging movements of a tube segment energized by e.g. a pump. Frequencies of tubing movements are given by the tubing lengths and harmonics thereof and by the beating between any frequencies involved, i.e. between different self-oscillations and pump frequencies. Mechanical fixation of the tube segments and other free components may be used to remove such mechanical resonances.

Still further, apart from the patient's heart, other physiological pulse generators in the patient may give rise to pressure pulses in the pressure signal. Generally, the physiological pulse generator may be one or more physiological phenomena such as reflexes, voluntary muscle contractions, non-voluntary muscle contractions, a heart, a breathing system, an autonomous system for blood pressure regulation and an autonomous system for body temperature regulation.

Embodiments of the invention relate to the monitoring carried out by the surveillance device 25, based on the monitoring signal. Specifically, the monitoring aims at detecting a disruption of the connection system C between the circuit 20 and the vascular system of the patient, i.e. on either the venous-side or the arterial-side, or both. The disruption may be caused by a dislodgement of the venous or arterial access device 1, 14 from the blood vessel access, i.e. that the access device 1, 14 comes loose from the vascular system of the patient. Alternatively, the disruption may be caused by a disconnection of the venous or arterial access device 1, 14 from the circuit 20, typically by disruption/defective coupling/uncoupling of the connectors C1a, C1b and C2a, C2b, respectively.

As explained above, each monitoring signal may be a time-dependent pressure signal which is derived from the data samples acquired from at least one of the pressure sensors 4a-4c, such as the pressure signal in FIG. 2(a). In the context of extracorporeal treatment, the monitoring signal includes one or more pressure pulses from the blood pump 3 and other repetitive pulse sources in the extracorporeal circuit (collectively denoted "pump pulses" in the following), as well as one or more pressure pulses originating from the patient (collectively denoted "physiological pulses" in the following). A monitoring signal containing both pump pulses and physiological pulses is also denoted "composite signal" in the following.

II. Monitoring Disruption of Connection System

Figure 3A:
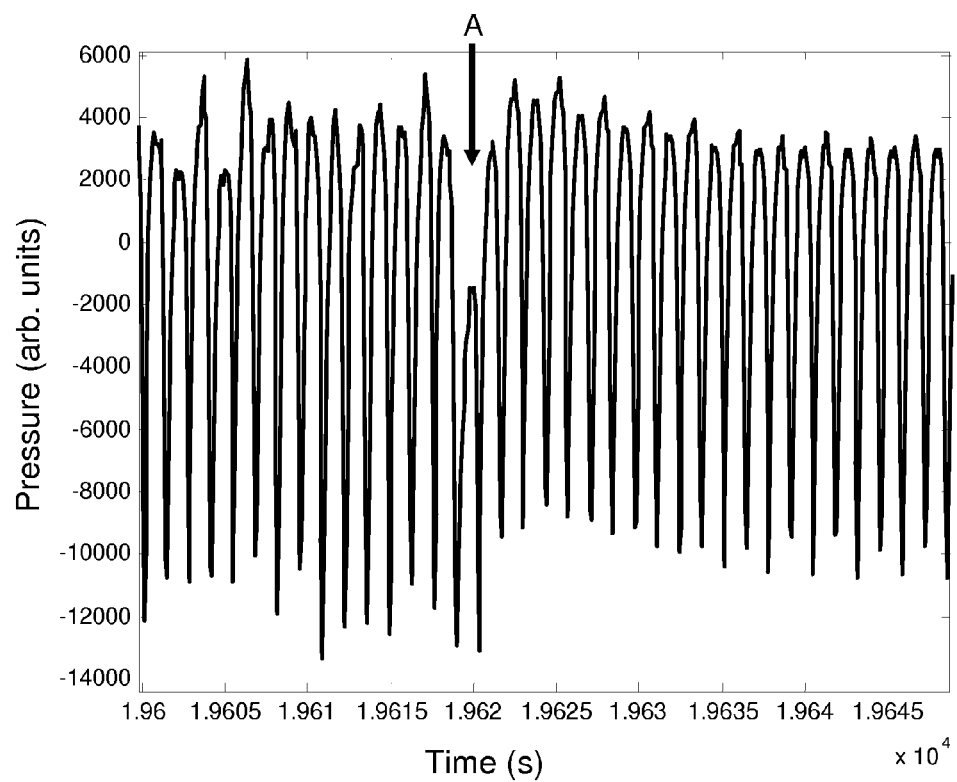
FIG. 3(a) is a plot of a pressure signal obtained from a venous pressure sensor in the system of FIG. 1.
Figure 3B:
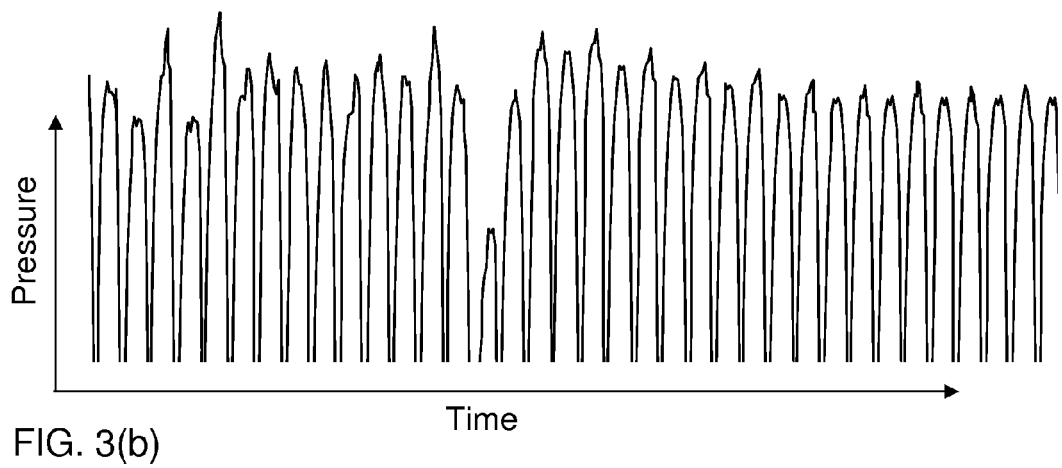
FIG. 3(b) is an enlarged view of the signal in FIG. 3(a).

The present Assignee has realized that a disconnection of extracorporeal circuit 20 from the vascular system of the patient is reflected in the distribution of signal values in the above-mentioned composite signal obtained from the output of the venous or arterial pressure sensor 4c, 4a in the extracorporeal circuit 20. FIG. 3(a) illustrates a composite signal obtained from the venous pressure sensor 4c in the extracorporeal circuit 20 of FIG. 1 during blood treatment. The arrow A indicates the time of disruption of the connection system C. A careful inspection of the composite signal reveals that that there is a change in symmetry in the composite signal before and after the disruption. Specifically, the composite signal contains a sequence of "apparent pulses", which are pressure pulses formed by a superposition of pump pulses and physiological pulses when the connection system C is intact, i.e. when a fluid connection is established between the circuit 20 and the vascular system of the patient. The change of symmetry occur between the apparent pulses in the composite signal. This may be seen even more clearly in the enlarged view of FIG. 3(b). The present Assignee has found that, before disruption, the composite signal is dominated by pump pulses, i.e. the apparent pulses a predominantly caused by pump pulses, but the shape of the pump pulses are modified by physiological pulses. The disruption changes the propagation path for the pressure waves caused by one or more physiological pulse generators in the patient, such that the physiological pulses decrease in magnitude, or even vanish, at the relevant pressure sensor 4c, 4a. In the example of FIG. 3, the apparent pulses in the composite signal, after disruption, are mainly (or exclusively) pump pulses which thus originate from the pulse sources in the extracorporeal circuit 20. The signal values of the apparent pulses after disruption thus have a more or less known or predictable distribution, e.g. in terms of shape, magnitude and timing. Thus, by analysing the distribution of signal values in the composite signal, it is e.g. possible to detect a dislodgement of one of the access devices 1, 14, or both. This type of disruption detection is also denoted "composite signal analysis" in the following.

The composite signal analysis may be applied whenever the physiological pulses are detectable in the composite signal with an intact connection system C between the circuit 20 and the patient. It is currently believed that the composite signal analysis is particularly suited for monitoring whenever the magnitude (e.g. peak-to-peak amplitude) of the physiological pulses are at least 2%, preferably at least 5%, and most preferably at least 10% of the magnitude of the pump pulses, as detected by the pressure sensor 4a, 4c. It should be noted that the physiological pulses may originate from only one of the above-mentioned physiological pulse generators, or a combination of such pulse generators, e.g. a combination of pulses from the patient's heart and breathing system.

It should be noted that the "superposition" of physiological pulses on pump pulses does not imply any fixed relation between the physiological pulses and the pump pulses. Thus, the physiological pulses need not combine with every pump pulse, nor does the physiological pulse have to combine with the pump pulses at any given timing. It is quite possible that certain pump pulses fall between pump pulses.

In one implementation, the monitoring signal is formed by the measurement data ("raw data") acquired from the pressure sensor, optionally pre-processed for removal of offset, high frequency noise and supply voltage disturbances, etc. It is also conceivable that such pre-processing removes specific parts of the pump pulses and/or the physiological pulses. For example, it may be desirable to remove pulse components caused by switching of mechanical valves, swinging movement of tube segments, operation of a pump for dialysis fluid, etc. The pre-processing may also involve a downsampling of the acquired data samples. Irrespective of implementation, the monitoring signal is a composite signal, which contains both pump pulses and physiological pulses.

The composite signal analysis offers a monitoring technique which may replace or supplement any known technique for monitoring the integrity of a connection system C, such as the techniques discussed in the Background section.

Figure 4:
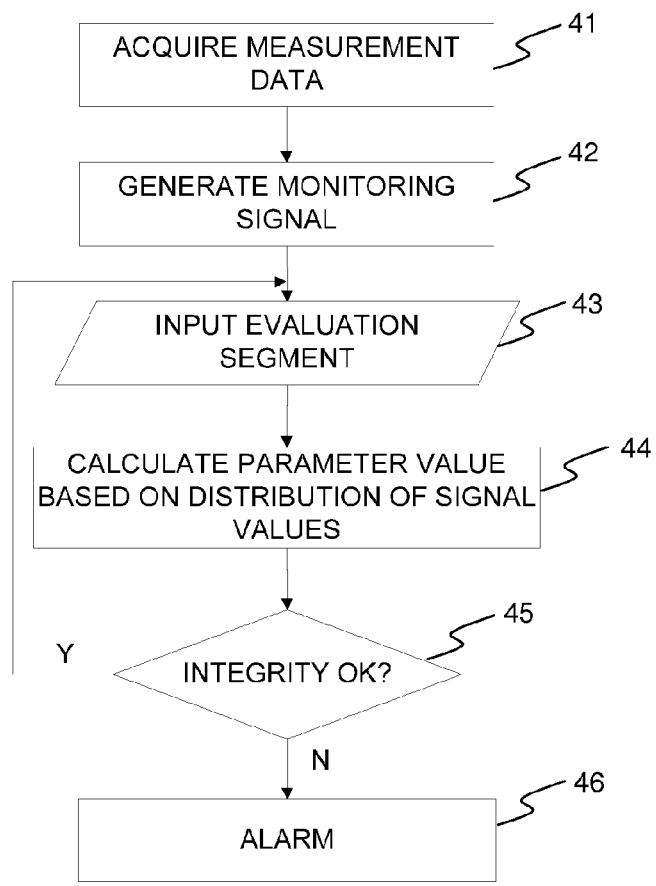
FIG. 4 is a flow chart of a process for monitoring fault conditions in a connection system.

FIG. 4 illustrates a monitoring process that includes an embodiment of the composite signal analysis. In step 41, measurement data is acquired from one of the pressure sensors 4a-4c in the circuit 20. In step 42, the measurement data is processed to form a monitoring signal. In step 43, an evaluation segment is extracted from the monitoring signal. The evaluation segment represents a time window in the monitoring signal. Subsequently, in step 44, the evaluation segment is processed for calculation of a parameter value based on a pulse feature of at least one of the apparent pulses in the monitoring signal, such that the parameter value represents a disturbance caused by the superposition of the physiological pulses on the pump pulses. In step 45, the parameter value is evaluated for determining the integrity of the connection system C. The evaluation step 45 may be designed to indicate disconnection/disruption whenever a single parameter value falls outside a given range, or below/above a given threshold, as applicable. Alternatively, the evaluation may require a given number, or a given fraction, of consecutive parameter values to fall outside a given range (or below/above a threshold) before indicating disconnection/disruption.

If the evaluation step 45 indicates disruption, the process proceeds to step 46 in which an alarm is issued (and/or the blood flow is stopped). Otherwise, the process returns to step 43 for extraction of subsequent evaluation segment from the monitoring signal.

For continuous surveillance, steps 41 and 42 may operate continuously to generate the monitoring signal, such that a time sequence of parameter values may be calculated based on extracted evaluation segments in the monitoring signal (steps 43-44). Each evaluation segment is typically selected such that it contains or represents at least part of a pump pulse and at least part of a physiological pulse if the connection system C is intact. Depending on the type of parameter, as will be exemplified below, the evaluation segment may be selected to contain/represent at least part of a physiological pulse in combination with part of a pump pulse, an entire pump pulse or a plurality of pump pulses. In all embodiments, the evaluation segments may be overlapping or non-overlapping in time.

Calculation of Parameter Value (Step 44)

In the following, the calculation of the parameter value according to step 44 will be further exemplified.

As noted above, the parameter value is designed to represent the disturbance caused by the superposition of the second pulses on the first pulses and is based on a pulse feature of one or more apparent pulses in the composite signal. Depending on implementation, the pulse feature may be one of a magnitude feature, a timing feature and a shape feature of the apparent pulse.

As will be further explained below, the pulse feature may be identified in the evaluation segment based on external timing information ("assisted identification"). The external timing information typically indicates the timing of the pump pulses in the evaluation segment, whereby each pulse feature may be identified at or around a time point that corresponds to a pump pulse in the evaluation segment(s). Alternatively or additionally, the pulse feature may be identified in the evaluation segment based solely on the signal values, i.e. the signal values "as such", in the evaluation segment ("inherent identification")

Figure 5:
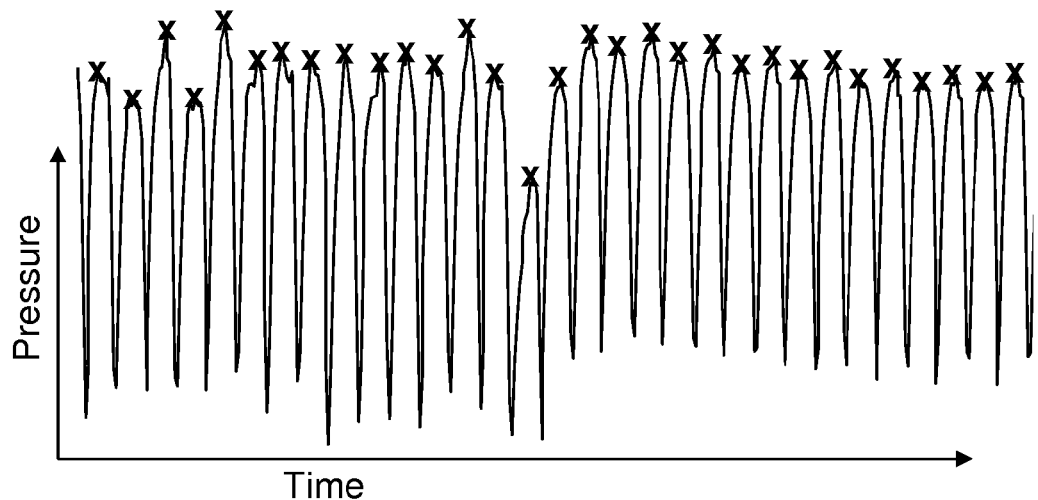
FIG. 5 is a plot to indicate local maxima in the pressure signal in FIG. 3(b).

In inherent identification, the magnitude of apparent pulses may, e.g., be given by peak values extracted from the monitoring signal. The peak value may be a local maximum and/or minimum, which may be identified in the monitoring signal by processing the time-sequence of signal values using any known technique, such as a first or second derivative test or thresholding. It may be beneficial to low-pass filter the pressure signal, to remove high-frequency noise, before identifying the peak values. To further improve noise robustness, each extracted peak value may instead be calculated as an average or sum of the signal values forming each peak, e.g. including signal values within 10-25% of the peak value or within a given time range around the peak values. FIG. 5 shows an example of a sequence of local maxima (indicated by x) that are determined for the signal in FIG. 3(b). In a variant, the magnitude is given by an amplitude value, e.g. a difference between a local maximum and a local minimum in the signal. In another variant, the magnitude is given by an area measure that represents the integrated area of the apparent pulse, optionally with respect to a baseline.

In assisted identification, magnitude values may be extracted from the time-sequence of signal values based on the external timing information. For example, the magnitude value may be approximated by a signal value in the monitoring at a time point given by the external timing information, or by an average of signal values around such a time point. The timing information may e.g. be obtained from the pump sensor 26 or the control unit 23 (see FIG. 1). Alternatively, the timing information may be calculated from measurement data acquired from another pressure sensor in the circuit 20.

In inherent identification, the timing of the apparent pulse may e.g., be given by the time point of any sufficiently well-defined signal feature of the apparent pulse in the monitoring signal, such as the above-mentioned peak value, a crossing point with a given signal level (e.g. zero), a leading edge, a trailing edge, etc.

In inherent as well as assisted identification, the shape feature may, e.g., be given directly or indirectly by the temporal signal profile of the respective apparent pulse, or part thereof. In one embodiment, such a shape feature is made up of the signal values of the apparent pulse in the monitoring signal. In a variant, the shape feature may be given by a curve fitted to the signal values. In yet another variant, the shape feature may be a similarity measure (such as a correlation value, see discussion in respect of pulse-to-pulse symmetry measures, below), which may be obtained by matching the apparent pulse to a reference pulse (e.g. a reference profile of pump pulses, see Section III). In inherent identification, shape feature may be extracted in a fixed time window around the aforesaid well-defined signal feature (e.g. around the peak value, or extending from the leading/trailing end), or it may be extracted as a function of two of more well-defined signal features (e.g. extending between the leading and trailing ends). In assisted identification, shape feature may extracted in a fixed time window around a time point given by the external timing information, optionally in combination with the one or more well-defined signal features that are identified in the monitoring signal.

In one specific example, a "center of gravity" measure is calculated for the evaluation segment or the apparent pulse (s) therein. As is well-known to the skilled person, the center of gravity is a measure that represents the average location of the weight of an object. Any known calculation algorithm may be used, and the center of gravity may be obtained as a pair of coordinates defined in term of magnitude and timing, respectively. Either, or both, of these coordinates may be used for calculating the parameter value.

In another specific example, a "moment of inertia" measure is calculated for the evaluation segment or the apparent pulse(s) therein. As is well-known to the skilled person, the moment of inertia is a measure that represents an object's resistance to changes to its rotation. The moment of inertia is calculated with respect to a given axis of rotation, which may be given by any sufficiently well-defined signal feature of the apparent pulse in the monitoring signal, such as the above-mentioned peak value, a crossing point with a given signal level (e.g. zero), a leading edge, a trailing edge, the above-mentioned center of gravity, etc. The moment of inertia I may be calculated as:

$$I = \sum_{i=1}^{n} m_i r_i^2,$$

where $m_i$ is an area element in the evaluation segment/apparent pulse and $r_i$ is the distance from the area element to the axis of rotation. It should be realized that there are other equivalent ways of calculating the inertia measure I. The inertia measure I is a hybrid pulse feature that represents both amplitude and timing of the apparent pulse.

In a variant, any one of the magnitude, timing and shape features may be identified in an envelope obtained from the monitoring signal. The envelope may, e.g., be obtained by applying a linear, time-invariant filter known as a Hilbert transformer to a set of signal values (signal segment) s in the monitoring signal. This operation results in a transformed signal segment ŝ, which is a 90° phase-shifted version of the signal segment s. The envelope b(n) may then be derived from $b(n) = \sqrt{s^2(n) + \hat{s}^2(n)}$, with n denoting time steps in the signal segments.

For improved processing efficiency, an approximate envelope may be calculated from the signal segment s based on the relation $$\hat{b}(n) = |s(n)| + \frac{2}{\pi}|s(n+1) - s(n)|.$$

In another variant, the envelope is obtained by calculating the sum of signal values within an integration time window, which is selected to contain a plurality of signal values while being smaller than the spacing of pump pulses. By sliding the integration time window along the monitoring signal, and calculating the sum for each of a number of partially overlapping integration time windows, the resulting sequence of sums will approximate the envelope of the monitoring signal. Other conventional techniques are available for extracting the envelope.

Figure 6:
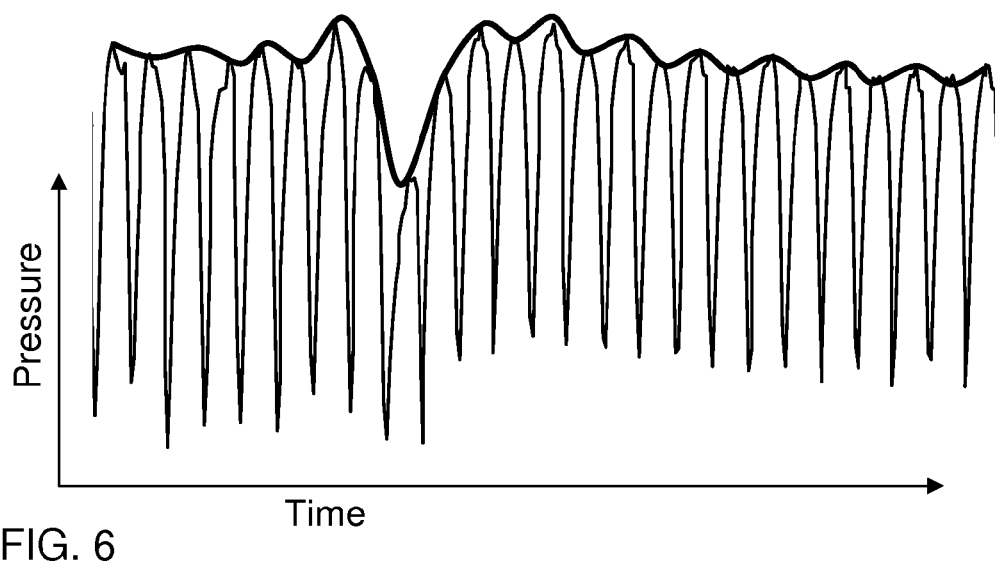
FIG. 6 is a plot to illustrate an envelope curve fitted to the pressure signal in FIG. 3(b).

FIG. 6 shows an example of an approximate envelope (indicated by a thick solid line) which is calculated by spline interpolation of the peak values shown in FIG. 5.

Below follows different examples of the step of calculating a parameter value based on the above-described pulse features. The following examples fall into three different categories: statistical dispersion measures, pulse-to-pulse symmetry measures, and pump pulse matching measures. In the following examples, the parameter value is a time domain measure that represents the disturbance caused by the superposition of physiological pulse(s) on pump pulse(s) within the evaluation segment. Unless otherwise stated, all measures may be calculated either directly from the monitoring signal or from an envelope as described above.

Statistical Dispersion Measures

In one embodiment of the first category, the parameter may be calculated as a statistical dispersion measure of a sequence of pulse features identified in the monitoring signal, whereby the parameter value reflects the variation in pulse feature within a time window in the monitoring signal.

Non-limiting examples of potentially useful statistical dispersion measures include standard deviation ($\sigma$), variance ($\sigma^2$), coefficient of variation, (defined as standard deviation-to-mean: $\sigma/\mu$), variance-to-mean ($\sigma^2/\mu$), skewness ($\mu_3/\sigma^3$), and kurtosis ($\mu_4/\sigma^4$), with $\mu_3$ and $\mu_4$ being the third and fourth moments about the mean $\mu$. Other examples include a sum of differences, e.g. given by $$\sum_{i=2}^{n} |x_i - x_{i-1}|, \text{ or } \sum_{i=1}^{n} \sum_{j=1}^{n} |x_i - x_j|,$$

or an energy measure, such as $$\sum_{i=1}^{n} x_i^2,$$

with n being the number of pulse features x within the time window. Yet other examples include a measure based on a sum of absolute differences from an average value m, with the average value m being calculated for the pulse features in the evaluation segment using any suitable function, such as arithmetic mean, geometric mean, median, etc. It is to be noted that all of the above suggested dispersion measures also include normalized and/or weighted variants thereof.

The pulse feature may be given by the above-mentioned magnitude feature (including the inertia measure), whereby the parameter value reflects the variation in apparent pulse magnitude within a time window in the monitoring signal.

Figure 7:
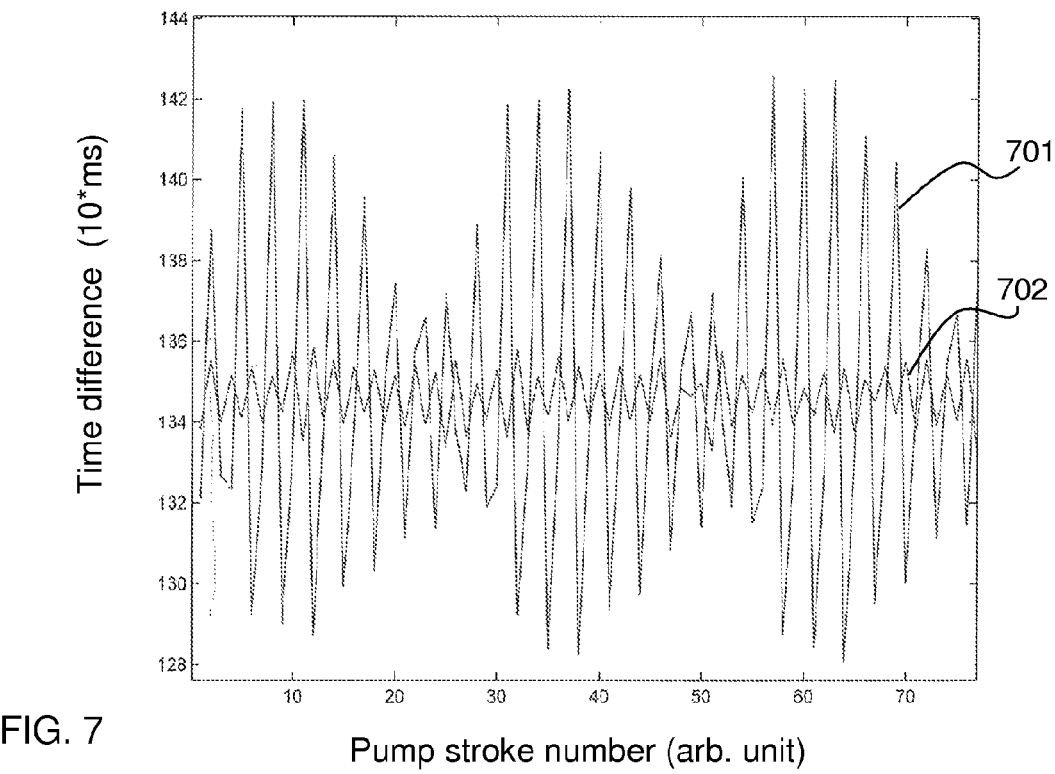
FIG. 7 is a plot of pulse-to-pulse time difference in pressure signals from pressure sensors in the system of FIG. 1.

Alternatively, the pulse feature may be given by the above-mentioned timing feature, provided that the timing feature is obtained by inherent identification. Thereby, the statistical dispersion measure may be calculated to reflect the variation in pulse-to-pulse timing in the monitoring signal. The pulse-to pulse timing may be given by the difference between timing features for pairs of pulses in the monitoring signal. For example, the pulse-to pulse timing may be given by the time difference between consecutive local maxima/minima in the monitoring signal (cf. FIG. 5). Any one of the above-mentioned statistical dispersion measures may be used to represent such a variation in timing. FIG. 7 illustrates the pulse-to-pulse timing as a function of pump stroke number. A first curve 701 represent time differences in the pressure signal from an arterial sensor (cf. 4a in FIG. 1) and a second curve 702 represent time differences in the pressure signal from a venous sensor (cf. 4c in FIG. 1) when the connection system C has been disrupted on the venous-side. As seen in FIG. 7, the pulse-to-pulse timing varies significantly more in the arterial pressure signal than in the venous pressure signal (as a result of the disturbance caused by the superposition of physiological pulses on pump pulses in the arterial pressure signal, which disturbance is essentially absent in the venous pressure signal).

Alternatively, the pulse feature may a shape feature, such as the above-mentioned similarity measure (e.g. correlation value) of the apparent pulse.

Figure 8:
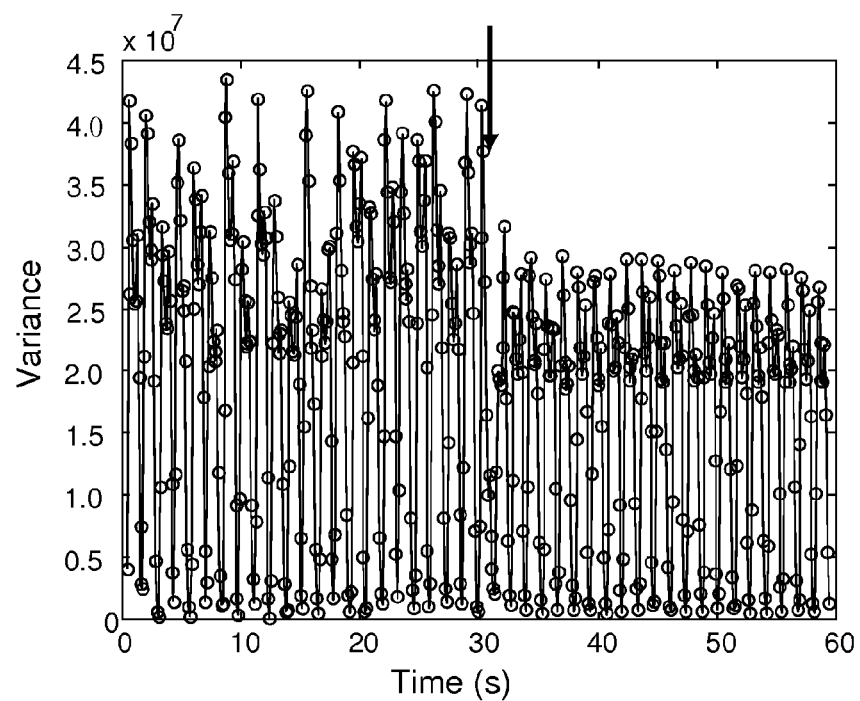
FIG. 8 is a plot of a variance measure as a function of time for the pressure signal in FIG. 3(b).

In another alternative, the parameter may be calculated as a statistical dispersion measure of the signal values in the monitoring signal, whereby the parameter value reflects the variation in signal values within a time window in the monitoring signal. Any of the above statistical dispersion measures may be used. Although such a parameter value is not explicitly based on any pulse feature identified in or extracted from the monitoring signal, the statistical dispersion measure is calculated for a time window in the monitoring signal and will thus represent the distribution of signal values in the time window. It is also to be noted that such a parameter value implicitly reflects a variation in magnitude within an apparent pulse, or across several apparent pulses, depending on the size of the time window. FIG. 8 illustrates variance calculated for a sequence of partially overlapping evaluation segments obtained from the monitoring signal in FIG. 3(a), wherein each evaluation segment corresponds to a time window of about 0.75 seconds. Consecutive evaluation segments overlap by 0.65 seconds. Clearly, by using the variance measure as a parameter, it may be possible to detect a disruption of the connection system some time after the time of disruption (arrow).

The second category is not limited to applying a statistical dispersion algorithm on pulse features or signal values in the evaluation segment. In a variant, a statistical calculation is instead made based on a time-sequence of parameter values, each calculated in an iteration of the monitoring process (steps 43-44 in FIG. 4) using any suitable measure, such as any of the measures described in relation to the first, second and third categories (i.e. a statistical dispersion measure a pulse-to-pulse symmetry measure or a pump pulse matching measure). The statistical calculation results in an aggregate parameter value which is evaluated in step 45, e.g. by comparing it to a threshold/range. The aggregate parameter value may be calculated using any of the above statistical dispersion measures, or be calculated as an average or sum of the parameter values.

Pulse-to-Pulse Symmetry Measures

In the second category, the parameter value is generated to directly reflect the pulse-to-pulse symmetry between the apparent pulses in the monitoring signal. In one embodiment, the parameter value is generated by comparing pairs of apparent pulses within the evaluation segment, or between evaluation segments, with the comparison being based on a specific pulse feature. During monitoring, the parameter value may thus be calculated by comparing a pulse feature of a current apparent pulse to the pulse feature of a preceding apparent pulse. As exemplified above, the pulse feature may e.g. relate to the magnitude, the timing or the shape of the respective apparent pulse.

If the pulse feature relates to timing, the parameter value may be given by the time difference between the pairs of pulses, e.g. given by the time difference between the above-mentioned well-defined signal features of the apparent pulses.

If the pulse feature relates to magnitude (including the inertia measure), the parameter value may be given by the difference in magnitude of the apparent pulses, or by the ratio of the magnitudes of the apparent pulses.

If the pulse feature relates to shape, and the pulse feature directly or indirectly represents the temporal signal profile of the respective apparent pulse, the parameter value may be formed by any known similarity measure (or equivalently, difference measure), including a correlation value between the temporal representations, a sum of differences between mutually aligned signal values in the temporal representations, and any suitable $L^n$-norm evaluated based on these differences, such as an $L^1$-norm (sum of absolute differences, aka Manhattan norm) or an $L^2$-norm (Euclidian norm). For calculation of the similarity measure, the temporal representations of the two apparent pulses may need to be aligned temporally, which may (but need not) be achieved by using the aforesaid timing information which is indicative of the timing of the pump pulses. The comparison of shape-related pulse features may or may not include an "autoscaling" between the temporal representations, in which the magnitude of one is adapted to the magnitude of the other, e.g. by minimizing a measure of the difference between the temporal representations, as is well-known in the art.

Figure 9:
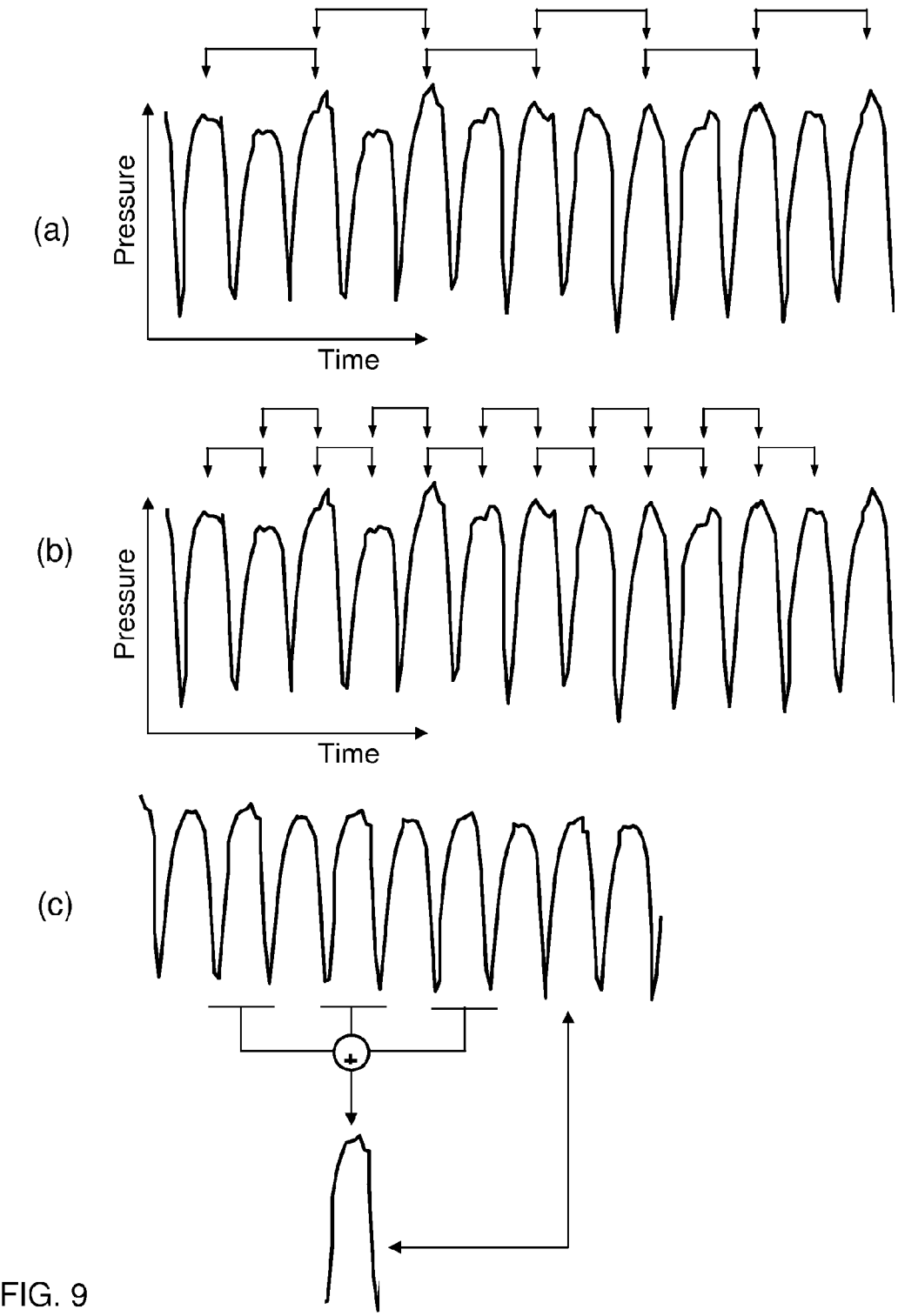
FIGS. 9(a)-9(c) are plots of pressure signals to illustrate calculation of pulse-to-pulse symmetry measures.

Irrespective of the type of pulse feature, the comparison may be made between apparent pulses that are known to be essentially identical, at least on average, in the absence of disturbances. In the example of a peristaltic pump, which generates a set of unique pump pulses for each revolution of its rotor, this may involve comparing corresponding apparent pulses associated with different revolutions of the rotor. FIG. 9(a) includes part of the pressure signal in FIG. 3 and indicates, by double-ended arrows, that pairs of apparent pulses are formed by every second pulse. In the illustrated example, the peristaltic pump generates a sequence of two unique pump pulses P1, P2 (see FIGS. 10-11 and related discussion below) for each revolution, and comparison is made between apparent pulses in the pressure signal that correspond to either P1 pulses or P2 pulses. When shape features are compared, however, it is also conceivable to compare groups of apparent pulses, which correspond to pump pulses, with each other. In the example of FIG. 9(a), such a group may be formed by apparent pulses corresponding to a consecutive pair of P1 and P2 pulses.

Alternatively, the comparison may be made for apparent pulses that have another known average relation to each other, in the absence of disturbances. FIG. 9(b) includes part of the pressure signal in FIG. 3 and indicates, by double-ended arrows, that pairs of apparent pulses are formed by consecutive apparent pulses in the pressure signal. In the illustrated example, the comparison is made between apparent pulses corresponding to P1 and P2 pulses, respectively.

In a variant, the parameter value may be calculated by comparing pulse features for pairs of pulses within the monitoring signal, and by aggregating the results of the individual comparisons. For example, the parameter value may be generated by evaluating any of the above-mentioned statistical dispersion measures on the results, or by calculating the average or sum of the results.

In a variant, the pulse feature is extracted from the evaluation segment and compared with a time average of a corresponding pulse feature obtained from one or more preceding apparent pulses within the same evaluation segment, or in one or more preceding evaluation segments. The pulse feature may be any one of magnitude, timing and shape. FIG. 9(c) illustrates an example involving a shape feature. Here, the time average of the pulse shape is calculated by combining (e.g. by temporally aligning and summing) temporal representations of three preceding apparent pulses based on the aforesaid timing information. Then, the parameter value is calculated by comparing a current pulse shape in the monitoring signal with the time average. It is to be understood that the selection of every second apparent pulse in FIG. 9(c) is merely intended as an example, and also that the time average may be formed by combining any number of temporal representations. It may also be noted that the evaluation of the parameter value may differ depending on the relation between the frequency of pump pulses and the frequency of physiological pulses in the monitoring signal. For example, in relation to the example of FIG. 9(c), if the physiological pulses (e.g. heart pulses) are known to have a fixed (synchronous) timing in relation to the pump pulses, the time average will approximate the combined shape of a pump pulse and a physiological pulse. Thus, a similarity between the current pulse shape and the time average indicates an intact connection system C. If the physiological pulses are not synchronous with the pump pulses, the time average will approximate the shape of a pump pulse, at least for a time average calculated based on a large number of apparent pulses, and a similarity between the current pulse shape and the time average will indicate a disrupted connection system C.

Figure 10A:
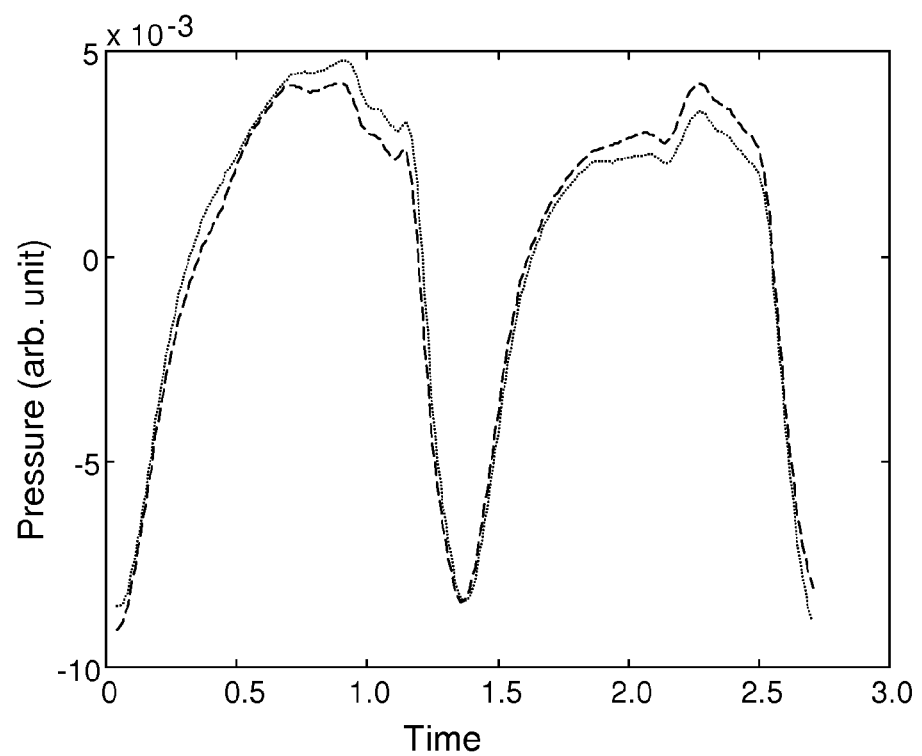
FIG. 10(a) is a plot of pressure pulses obtained for an intact connection system.
Figure 10B:
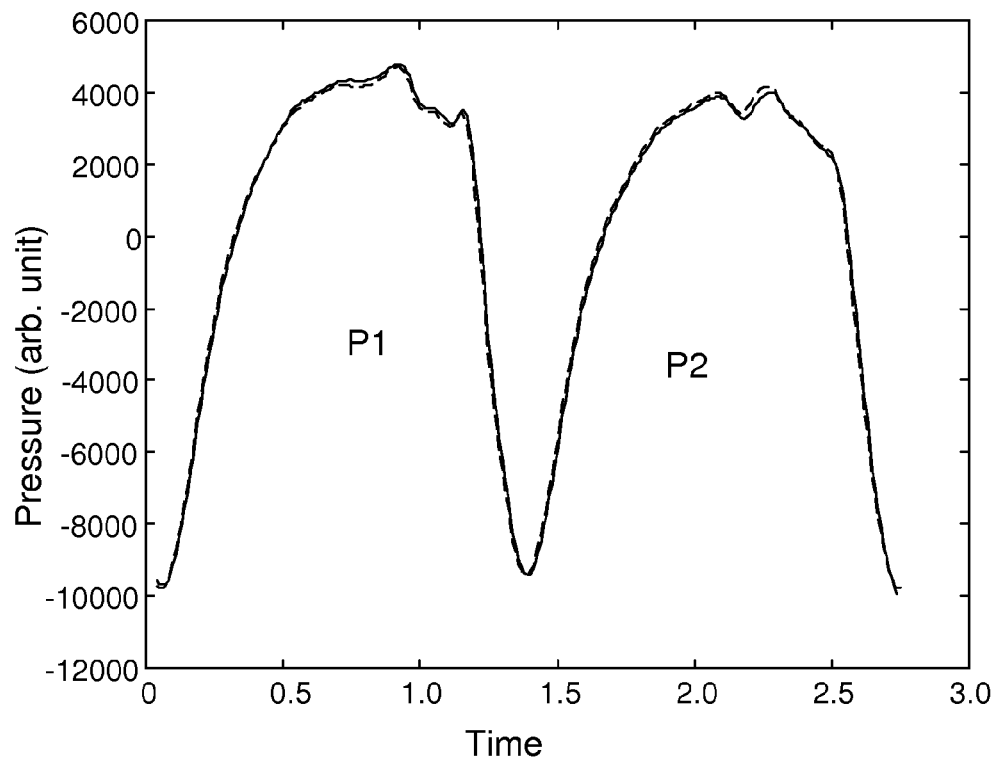
FIG. 10(b) is a plot of pressure pulses obtained for a disrupted connection system.
Figure 10C:
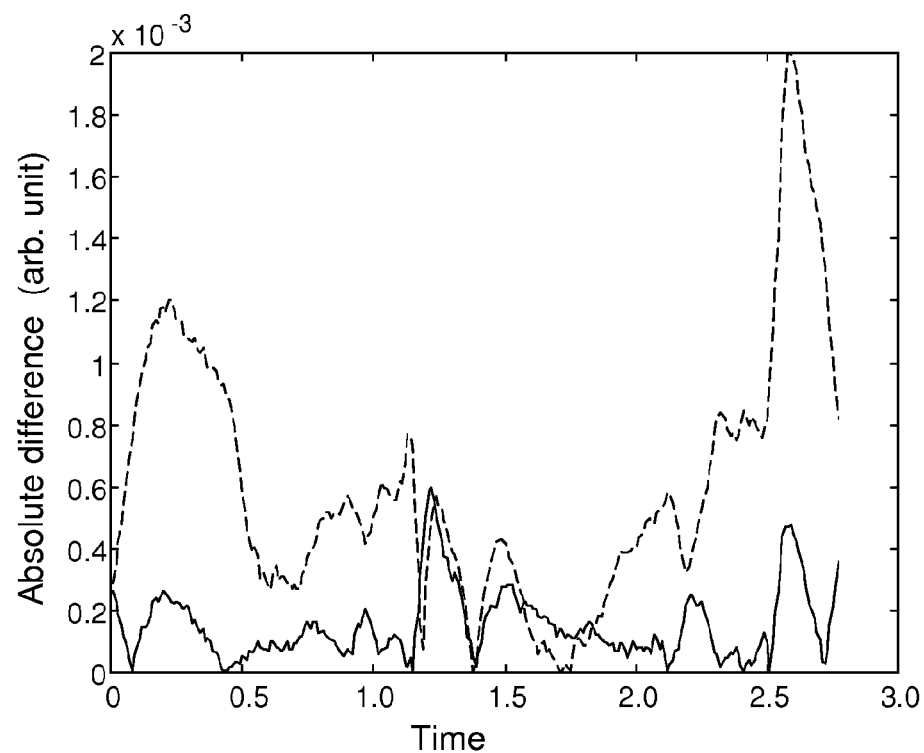
FIG. 10(c) is a plot of absolute difference between the pressure pulses in FIG. 10(a) and FIG. 10(b), respectively.

To further illustrate the effectiveness of pulse-to-pulse symmetry measures, FIG. 10(a) is a plot of two groups of apparent pulses corresponding to P1 and P2 pulses, where the two groups are obtained at different times in a pressure signal when the connection system C is intact, and FIG. 10(b) is a plot of two groups of apparent pulses corresponding to P1 and P2 pulses, where the two groups are obtained at different times in a pressure signal when the connection system C is disrupted. FIG. 10(c) is a plot of the absolute difference between the groups in FIG. 10(a) as a function of time (dashed line) and between the groups in FIG. 10(b) as a function of time (full line). Clearly, a disruption of the connection system C may be detected based on a change in symmetry between corresponding (groups of) apparent pulses in the pressure signal.

Pump Pulse Matching Measures

In the third category, the parameter value is generated in a matching procedure, in which a pulse feature in the form of shape data is extracted from the monitoring signal, which may be a pressure signal or an envelope as described in the foregoing. In the following, it is assumed that the monitoring signal is a pressure signal, and that the shape data is matched to predicted shape data for a pump pulse. If the pump generates more than one unique pump pulse, the predicted shape data may, but need not, represent a complete set of unique pump pulses.

As noted above, the shape data may directly or indirectly represent the temporal signal profile of one or more apparent pulses (or part thereof) in the evaluation segment. In one embodiment, the shape data may be made up of all or a subset of the signal values in the evaluation segment, and is thus a temporal representation of the actual shape of at least part of an apparent pulse in the evaluation segment (denoted "temporal shape data"). The temporal shape data may or may not be a downsampled or low-pass filtered version of the evaluation segment.

Figure 11:
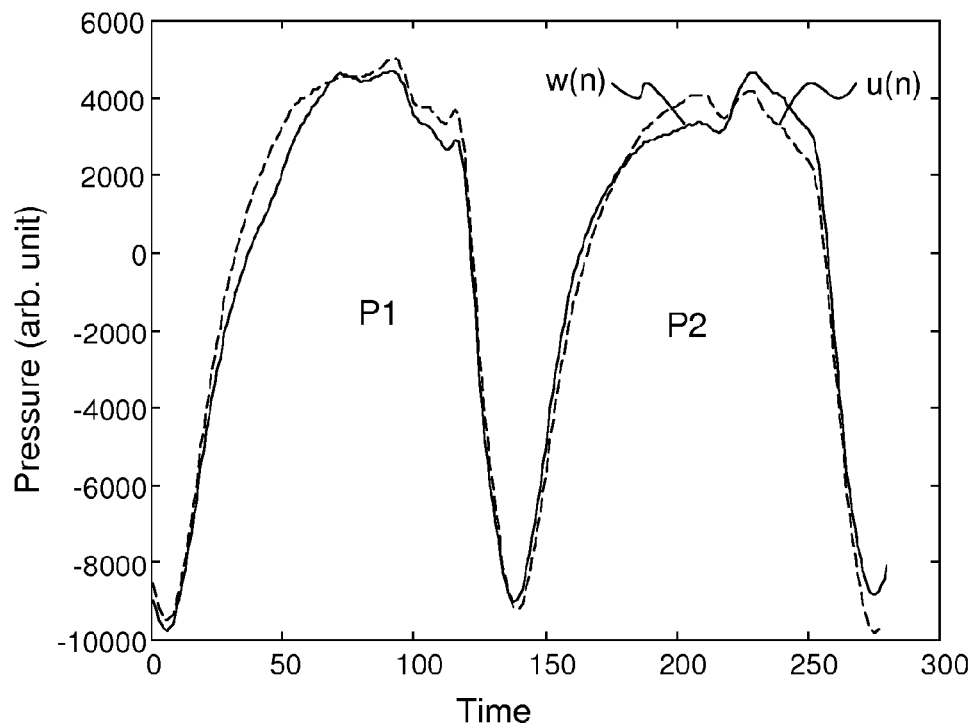
FIG. 11 is a plot of temporal shape data obtained from a pressure signal and corresponding reference profile of two consecutive pump pulses.

FIG. 11 illustrates temporal shape data w(n) obtained from an evaluation segment generated based on a pressure signal obtained from the venous pressure sensor 4c in the extracorporeal circuit 20 of FIG. 1, when the connection system C is intact. In this example, the temporal shape data w(n) comprises two apparent pulses that correspond to two pump pulses P1, P2, which are generated by a respective roller in the blood pump engaging a tubing segment in the peristaltic blood pump (cf. rollers 3a and 3b in FIG. 3). FIG. 11 also illustrates a temporal reference profile u(n) which represents the shape of the pump pulses P1, P2.

In another embodiment, the shape data is made up of spectral shape data, such as signal amplitude given as a function of frequency and/or signal phase given as a function of frequency. Such spectral shape data may be obtained by spectral analysis of the evaluation segment, e.g. via Fourier analysis or any equivalent technique. It should be noted that a complete representation of the shape of apparent pulse(s) in the evaluation segment would require the spectral shape data to include both the frequency distribution in amplitude and the frequency distribution in phase. In the context of the present application, however, either one of these frequency distributions is deemed to represent the shape of the evaluation segment and may thus be used to calculate the parameter value, by comparing the frequency distribution to a corresponding reference profile, which is given as a frequency distribution of signal amplitude or phase, as applicable (cf. FIGS. 16(a)-16(d) below).

The parameter value may represent the similarity or dissimilarity between the temporal or spectral shape data and one or more corresponding reference profiles. The parameter value may thus be derived by comparing or matching the shape data to the reference profile(s). If two reference profiles are used, one may represent an intact connection system and one may represent a disrupted connection system. The comparing/matching may thus result in two parameter values, which may be evaluated collectively (in step 45) to determine the integrity of the connection system. Although the following description assumes that only one reference profile is used, it is equally applicable to the use of two reference profiles.

In one embodiment, using temporal shape data, the parameter value is obtained by convolving or cross-correlating the temporal shape data w(n) and the temporal reference profile u(n), with the parameter value being given by a resulting correlation value, typically the maximum correlation value.

In another embodiment, using temporal shape data, the temporal shape data w(n) and the temporal reference profile u(n) are aligned with each other, such that the pulse(s) in the shape data and the reference profile overlap (e.g. as shown in FIG. 11), based on timing information which indicates the timing of the pump pulse(s) in the temporal shape data w(n). Such timing information may alternatively be implicit, e.g. if each evaluation segment is generated with known timing with respect to the pump pulses. In such a variant, the temporal shape data may be extracted and directly aligned with the temporal reference profile.

In an embodiment using the above-mentioned spectral shape data, spectral shape data may be directly aligned with a corresponding reference profile, since both the spectral shape data and the reference profile may be given within a known range of frequencies.

The comparing/matching process may or may not include an "autoscaling" between the shape data and reference profile, in which the magnitude of one is adapted to the magnitude of the other, e.g. by minimizing a measure of the difference between the shape data and the reference profile, as is well-known in the art.

The parameter value may be calculated as a correlation value, a sum of differences between mutually aligned signal values in the shape data and the reference profile, or any suitable $L^n$-norm evaluated based on these differences, such as an $L^1$-norm (sum of absolute differences, aka Manhattan norm) or an $L^2$-norm (euclidian norm). The skilled person realizes that any known difference or similarity measure may be evaluated and used as parameter value indicative of the shape of the apparent pulse(s).

Figure 12:
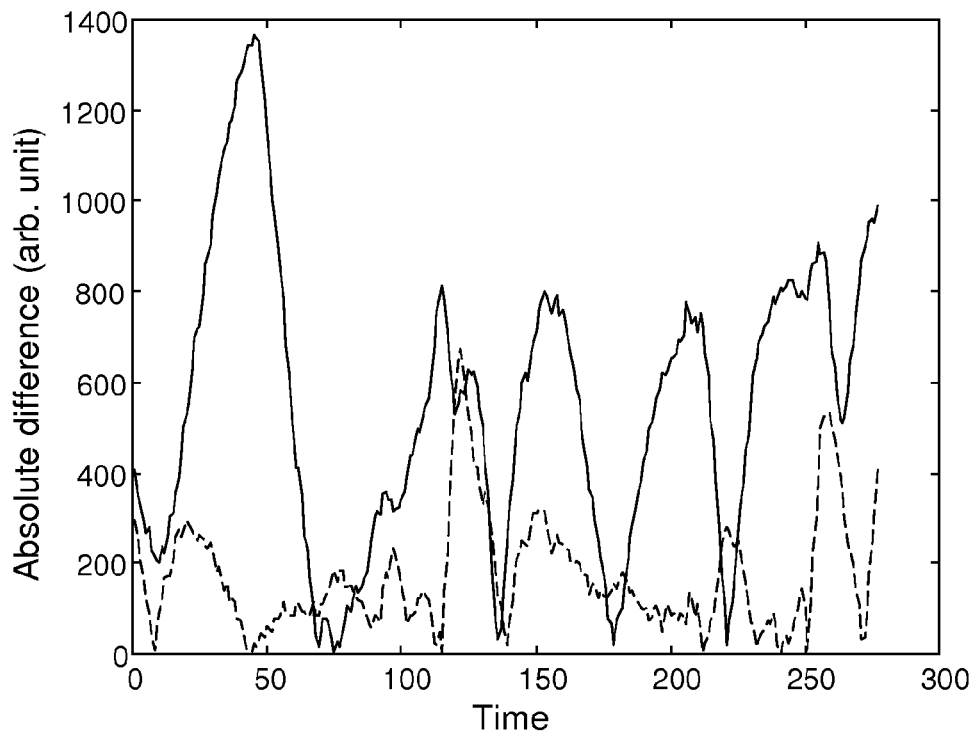
FIG. 12 is a plot of absolute difference as a function of time for the signals in FIG. 11.

FIG. 12 is a plot of the absolute difference (full line) between the temporal shape data w(n) and the temporal reference profile u(n) in FIG. 11, as a function of time within the shape data. For comparison, FIG. 12 also includes the absolute difference between the temporal shape data w(n) and the temporal reference profile u(n), when the connection system C is disrupted. Clearly, the disruption of the connection system C may be detected based on pump pulse matching measures.

It should be understood, though, that the temporal shape data may include a larger number of pulses than the reference profile, whereby each temporal shape data may be matched against several reference profiles, which may or may not be identical. For example, when the blood pump has a number of different pump strokes, each generating a unique pump pulse (cf. P1, P2 in FIGS. 10-11), the temporal shape data may be matched against a set of reference profiles representing the different pump pulses.

The above-described embodiments rely on the use of a reference profile (temporal or spectral) that properly represents the temporal profile of the pump pulse(s). The reference profile may be obtained in a reference measurement, based on measurement data acquired from one or more of the pressure sensors 4a-4c in the circuit 20, suitably by identifying and possibly averaging a set of pump pulses in the measurement data. During the reference measurement, the physiological pulses are either prevented from reaching the relevant pressure sensor, or they are removed by proper filtering of the measurement data. In another variant, the reference measurement may operate on measurement data from a pressure sensor which is substantially isolated from the physiological pulses. In such a situation, the reference profile may be obtained from the isolated sensor, and used for generating the reference profile (optionally after adjustment/modification for differences in confounding factors, see below), which is then used in the actual monitoring process. For example, the pressure signal from the system sensor 4b in the extracorporeal circuit 20 of FIG. 1 may be essentially isolated from the physiological pulses, and this pressure signal may thus be used in a reference measurement, while the actual monitoring process may operate on measurement data from either of the pressure sensors 4a-4c.

Alternatively, a predetermined (i.e. predefined) reference profile may be used, which optionally may be modified according to a mathematical model accounting for wear in the blood pump, blood flow rates, tubing dimensions, speed of sound in the blood, etc.

Different embodiments for predicting or estimating the reference profile in the extracorporeal circuit 20 of FIG. 1 are further described in Section III below.

The above-described matching procedure may also be operated on the envelope obtained from the monitoring signal, wherein the extracted shape data is matched to a temporal or spectral reference profile for the envelope (i.e. an "envelope reference profile"). Although Section III describes techniques for obtaining reference profiles for pressure signals, the skilled person should have no difficulty to derive an envelope reference profile by applying the techniques in Section III. For example, the temporal reference profile obtained in Section III may be processed for envelope extraction and then used as an envelope reference profile. In another embodiment, the envelope reference profile is given by a sinusoid with a frequency of 0.5 $f_0$, or a multiple thereof.

Evaluation of the Parameter Value (Step 45)

Below follows a description of some additional embodiments for obtaining the threshold/range which is used for evaluating the parameter value in step 45 (FIG. 4).

The threshold/range may be pre-set or predetermined, e.g. based on theoretical calculations or preceding experiments/tests. Such tests include obtaining a pressure signal from one of the pressure sensors 4a-4c in the extracorporeal circuit 20 during priming of the circuit, when the connection system C is either disconnected or intact.

Alternatively, the threshold/range may be derived during operation of the circuit 20, based on measurement data from another pressure sensor in the circuit 20, or from preceding signal values data from the pressure sensor that provides the measurement data for the monitoring signal.

For example, if the composite signal analysis aims at detecting disruption of the venous side of the connection system C, a pressure signal may be obtained from the venous pressure sensor while the venous side of the connection system C is intact and processed to calculate the parameter value, which is used for setting the threshold. In an alternative, if the composite signal analysis aims at detecting disruption of the venous side of the connection system C, a pressure signal may be obtained from the arterial pressure sensor while the arterial side of the connection system C is intact and be processed to calculate the parameter value, which is used for setting the threshold. In either example, the threshold may, e.g., be set to the calculated parameter value (or an aggregate of a sequence of calculated parameter values), optionally increased/decreased by a predefined amount/percentage.

In a specific example, the monitoring signal is generated based on measurement data from the venous sensor 4c, and the parameter value is calculated as a statistical dispersion measure. The threshold/range may be obtained, during monitoring, by calculating a corresponding statistical dispersion measure based on the measurement data from the arterial sensor 4a. Optionally, the threshold/range may be corrected for differences in the magnitude between the physiological pulses in the measurement data from the venous sensor 4c and the arterial sensor 4a, respectively. Such a difference in magnitude may be detected by intermittently stopping the blood pump 3 and analysing the measurement data from the sensors 4c, 4a. In this example, and generally for the present invention, the monitoring process may include logic that detects if both the parameter value and the threshold/range tend to decrease over time. Such a dual decrease may be caused by a disruption/disconnection of both access devices 1, 14 or by a reduction in magnitude of the physiological pulses, e.g. due to a reduced average pressure in the blood vessel access. Upon detection of a dual decrease, the logic may therefore stop the blood pump 3 and evaluate if there are any physiological pulses in the measurement data from one or both of the sensors 4a, 4c. If physiological pulses are not found, the logic may cause an alarm to be issued. Otherwise, the blood pump 3 may be started and the monitoring resumed, optionally using another monitoring technique.

III. Obtaining a Reference Profile of Pump Pulses

Generally, the reference profile is dependent on the operational state of the extracorporeal circuit 20. For example, if the rotation frequency of the blood pump 3 is changed, e.g. to change the blood flow rate through the circuit, the shape of the pump profile(s) will change. This effect may be addressed in different ways.

In a first embodiment, a reference measurement is carried out intermittently during treatment, so as to derive an updated reference profile to be used in the monitoring process until the next reference measurement. The reference measurement may be triggered by a change in the operational state of the circuit, or be carried out at regular time intervals.

Figure 13:
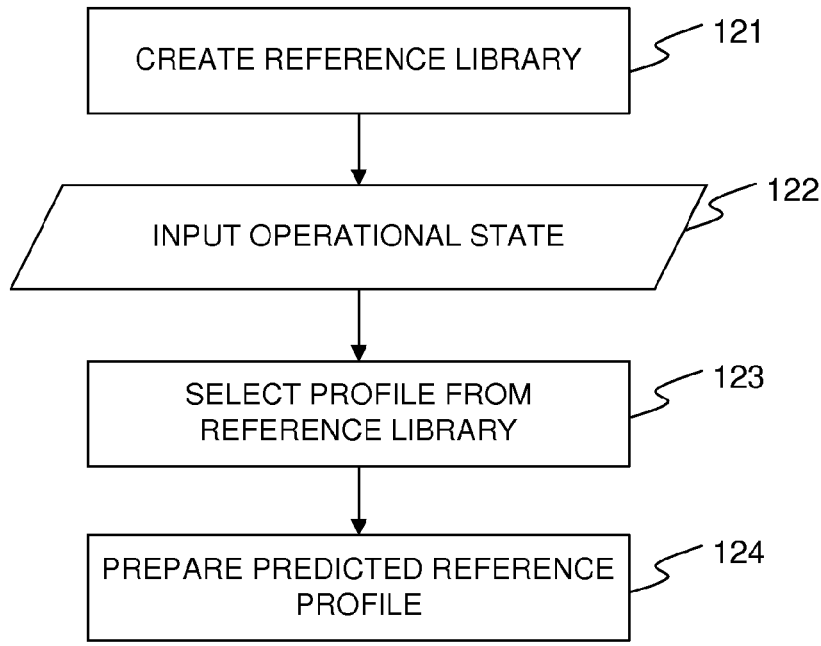
FIG. 13 is a flow chart of a process for obtaining a reference profile.

FIG. 13 is a flow chart of a second embodiment. In the second embodiment, a reference library or database is first created based on the reference measurement (step 121). The resulting reference library is typically stored in a memory unit, e.g. RAM, ROM, EPROM, HDD, Flash, etc, in the surveillance device 25. During the reference measurement, reference profiles (temporal or spectral) are acquired for a number of different operational states of the extracorporeal circuit 20. Each operational state is represented by a unique combination of system parameter values. For each operational state, a reference profile is generated to represent the temporal signal profile of the pump pulses. The reference profiles together with associated system parameter values are then stored in the reference library, which is implemented as a searchable data structure, such as a list, look-up table, search tree, etc. In the following, the profiles stored in the library are denoted "library profiles" to distinguish them from the reference profiles used in calculating the parameter value during the actual monitoring process.

During the actual monitoring process, current state information indicating the current operational state of the extracorporeal circuit is obtained from the system, e.g. from the pump sensor 26, the control unit 23 or otherwise (step 122). The current state information may include a current value of one or more system parameters. The current value is then matched against the system parameter values in the reference library. Based on the matching, one or more library profiles are selected (step 123) and used for preparing a predicted reference profile (step 124) for use in the monitoring process.

Generally, the aforesaid system parameters represent the overall system state, including but not limited to the structure, settings, status and variables of the extracorporeal circuit or its components. In the system of FIG. 1, exemplary system parameters may include:

Pump-Related Parameters: number of active pumps connected directly or indirectly (e.g. in a fluid preparation system for the dialyser) to the extracorporeal circuit, type of pumps used (roller pump, membrane pump, etc), flow rate, revolution speed of pumps, shaft position of pump actuator (e.g. angular or linear position), etc Dialysis machine settings: temperature, ultrafiltration rate, mode changes, valve position/changes, etc Disposable dialysis equipment/material: information on pump chamber/pump segment (material, geometry and wear status), type of blood line (material and geometry), type of dialyser, type and geometry of access devices, etc Dialysis system variables: actual absolute pressures of the system upstream and downstream of the blood pump, e.g. venous pressure (from sensor 4c), arterial pressure (from sensor 4a) and system pressure (from sensor 4b), gas volumes trapped in the flow path, blood line suspension, fluid type (e.g. blood or dialysis fluid), etc Patient status: blood access properties, blood properties such as e.g. hematocrit, plasma protein concentration, etc It is to be understood that any number or combination of system parameters may be stored in the reference library and/or used as search variables in the reference library during the monitoring process.

In the following, the second embodiment will be further explained in relation to a number of examples. In all of these examples, the pump revolution frequency ("pump frequency"), or a related parameter (e.g. blood flow rate) is used to indicate the current operational state of the extracorporeal circuit during the monitoring process. In other words, the pump frequency is used as search variable in the reference library. The pump frequency may e.g. be given by a set value for the blood flow rate output from the control unit 23, or by an output signal of the pump sensor 26. Alternatively, the pump frequency may be obtained by frequency analysis of the pressure signal from any of the sensors 4a-4c during operation of the fluid system. Such frequency analysis may be achieved by applying any form of harmonics analysis to the pressure signal, such as Fourier or wavelet analysis. As indicated in FIG. 2(b), the base frequency $f_0$ of the pump may be identified in a resulting power spectrum In the following, three examples are given of techniques for generating a predicted reference profile by accessing such a reference library.

Figure 14:
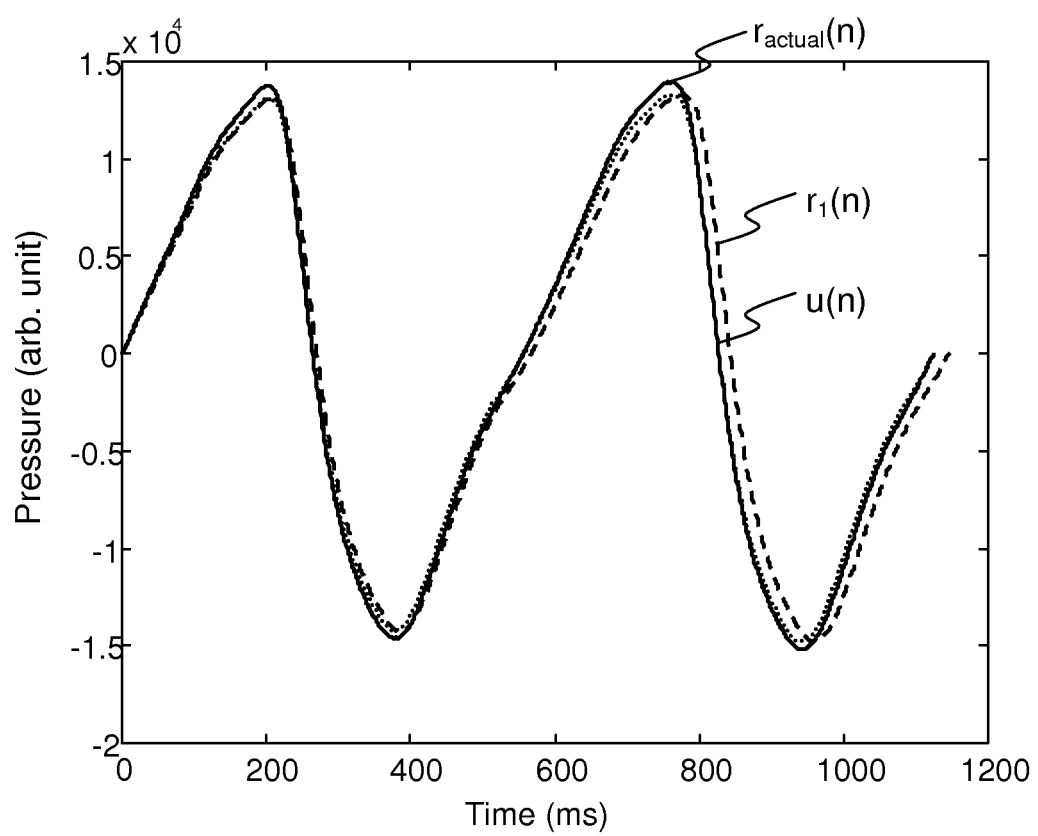
FIG. 14 is a plot to illustrate an extrapolation process for generating a reference profile.

In a first example, the library profiles stored in the reference library are temporal profiles. The reference library is searched for retrieval of the library profile that is associated with the pump frequency that lies closest to the current pump frequency. If no exact match is found to the current pump frequency, an extrapolation process is executed to generate the predicted reference profile. In the extrapolation process, the retrieved library profile is scaled in time to the current pump cycle, based on the known difference ("pump frequency difference") between the current pump frequency and the pump frequency associated with the retrieved library profile. The amplitude scale may also be adjusted to compensate for amplitude changes due to pump frequency, e.g. based on a known function of amplitude as a function of pump frequency. FIG. 14 illustrates a library profile $r_i(n)$ obtained at a flow rate of 470 ml/min, and a predicted reference profile u(n) which is obtained by scaling the library profile to a flow rate of 480 ml/min. For comparison only, a measured reference profile $r_{actual}(n)$ at 480 ml/min is also shown, to illustrate that extrapolation process indeed may yield a proper estimation of the reference profile.

In a second example, the library profiles stored in the reference library are temporal profiles. The reference library is again searched based on current pump frequency. If no exact match is found to the current pump frequency, a combination process is executed to generate the predicted reference profile. Here, the library profiles associated with the two closest matching pump frequencies are retrieved and combined. The combination may be done by re-scaling the pump cycle time of the retrieved library profiles to the current pump frequency and by calculating the predicted reference profile via interpolation of the re-scaled library profiles. For example, the estimated reference profile u(n) at the current pump frequency v may be given by:

$$u(n)=g(v-v_i)\cdot r_i(n)+(1-g(v-v_i))\cdot r_j(n),$$

wherein $r_i(n)$ and $r_j(n)$ denotes the two retrieved library profiles, obtained at a pump frequency $v_i$ and $v_j$, respectively, after re-scaling to the current pump frequency v, and g is a relaxation parameter which is given as a function of the frequency difference $(v-v_i)$, wherein $v_i \leq v \leq v_j$ and $0 \leq g \leq 1$. The skilled person realizes that the predicted reference profile u(n) may be generated by combining more than two library profiles.

Figure 15A:
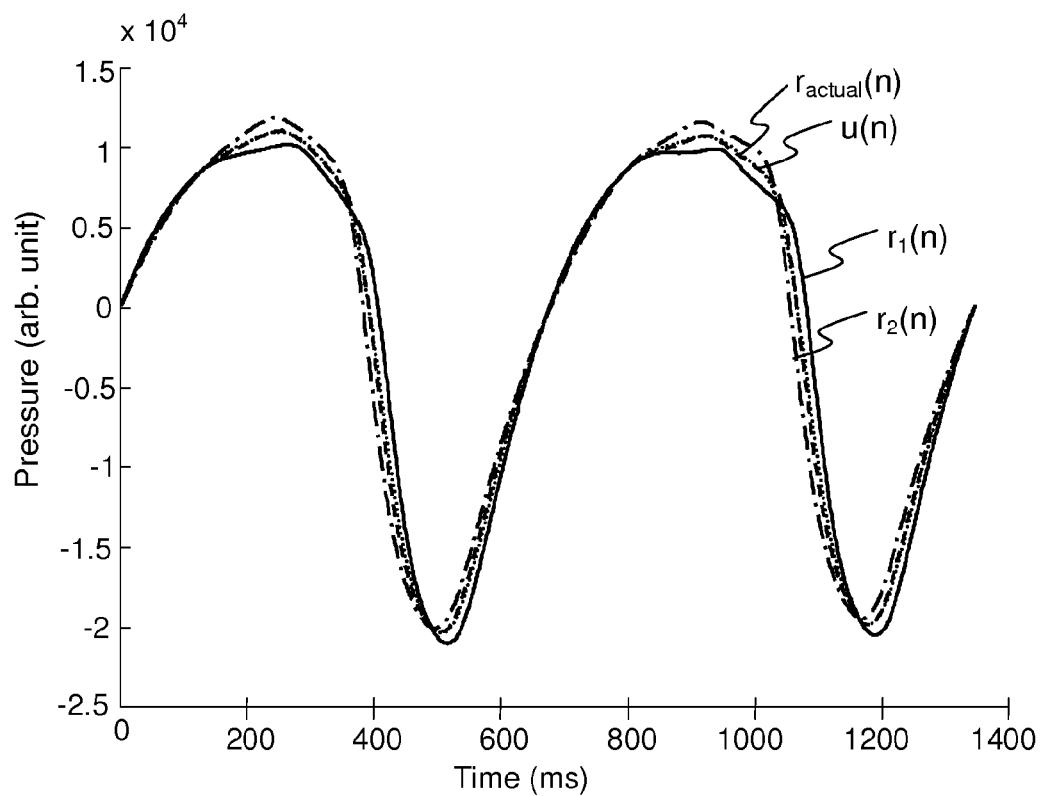
FIG. 15(a) is a plot to illustrate an interpolation process for generating a reference profile.
Figure 15B:
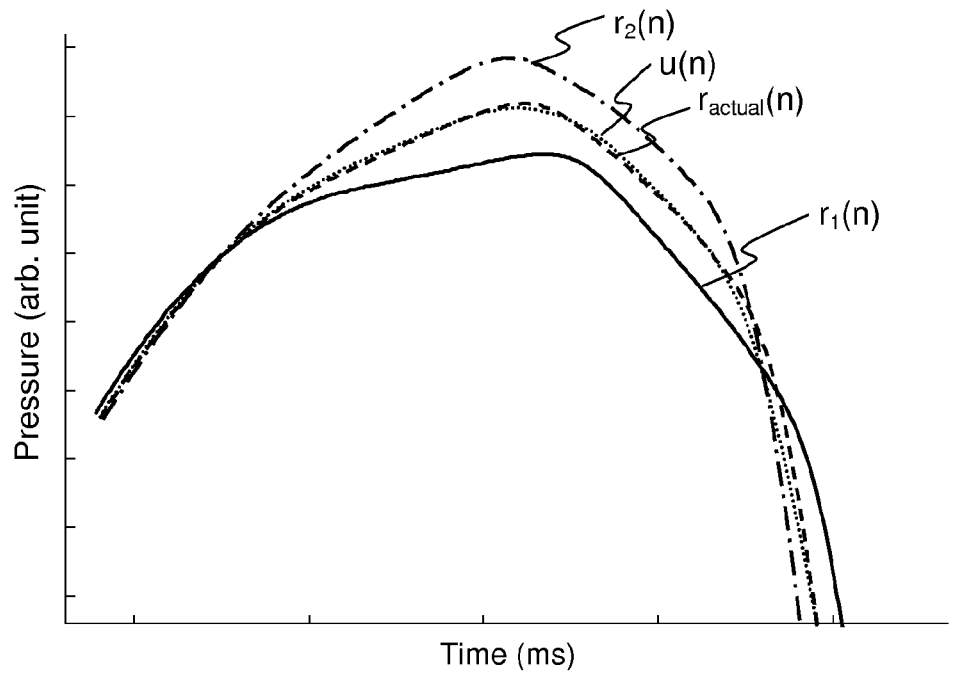
FIG. 15(b) is an enlarged view of FIG. 15(a).

FIG. 15(a) illustrates a predicted reference profile u(n) at a current flow rate of 320 ml/min for measurement data obtained from the venous sensor 4c in the system of FIG. 1. The predicted reference profile u(n) has been calculated as an average of a library profile $r_1(n)$ obtained at a flow rate of 300 ml/min from the venous sensor and a library profile $r_2(n)$ obtained at a flow rate of 340 ml/min from the venous sensor. For comparison only, a measured reference profile $r_{actual}(n)$ at 320 ml/min is also shown, to illustrate that the combination process indeed may yield a properly predicted reference profile. In fact, the differences are so small that they are only barely visible in the enlarged view of FIG. 15(b).

The first and second examples may be combined, e.g. by executing the extrapolation process of the first example if the pump frequency difference is less than a certain limit, and otherwise executing the combination process of the second example.

In a third embodiment, like in the second embodiment shown in FIG. 13, a number of reference signals are acquired in the reference measurement, wherein each reference signal is obtained for a specific combination of system parameter values. The reference signals are then processed for generation of reference spectra, which are indicative of the energy and phase angle as function of frequency. These reference spectra may e.g. be obtained by Fourier analysis, or equivalent, of the reference signals. Corresponding energy and phase data (i.e. spectral profiles) are then stored in a reference library together with the associated system parameter values (cf. step 121 in FIG. 13). The implementation of the reference library may be the same as in the second embodiment.

During the actual monitoring process, a current value of one or more system parameters is obtained from the extracorporeal circuit (cf. step 122 in FIG. 13). The current value is then matched against the system parameter values in the reference library. Based on the matching, a specific set of energy and phase data may be retrieved from the reference library to be used for generating the predicted reference profile (cf. step 123 in FIG. 13). The predicted reference profile may be temporal and may be generated by adding sinusoids of appropriate frequency, amplitude and phase, according to the retrieved energy and phase data (cf. step 124 in FIG. 13). Alternatively, the predicted reference profile may be spectral, for matching against spectra shape data.

Generally speaking, without limiting the present disclosure, it may be advantageous to generate a predicted temporal reference profile from energy and phase data when the pump pulses (to be analysed in the monitoring process) is expected to contain only one or a few base frequencies (and harmonics thereof), since the predicted temporal reference profile may be represented by a small data set (containing energy and phase data for the base frequencies and the harmonics). On the other hand, when the power spectrum of the pump pulses is expected to be more complex, e.g. a mixture of many base frequencies, it may instead be preferable to generate the predicted temporal reference profile from one or more library profiles.

Figure 16A:
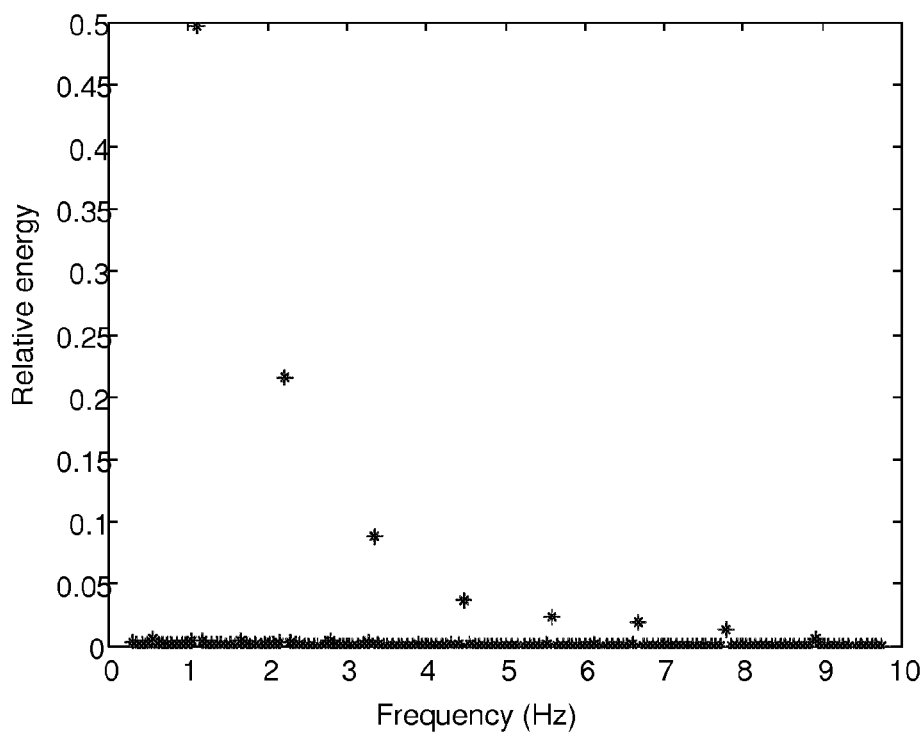
FIG. 16(a) represents a frequency spectrum of pump pulses at one flow rate.
Figure 16B:
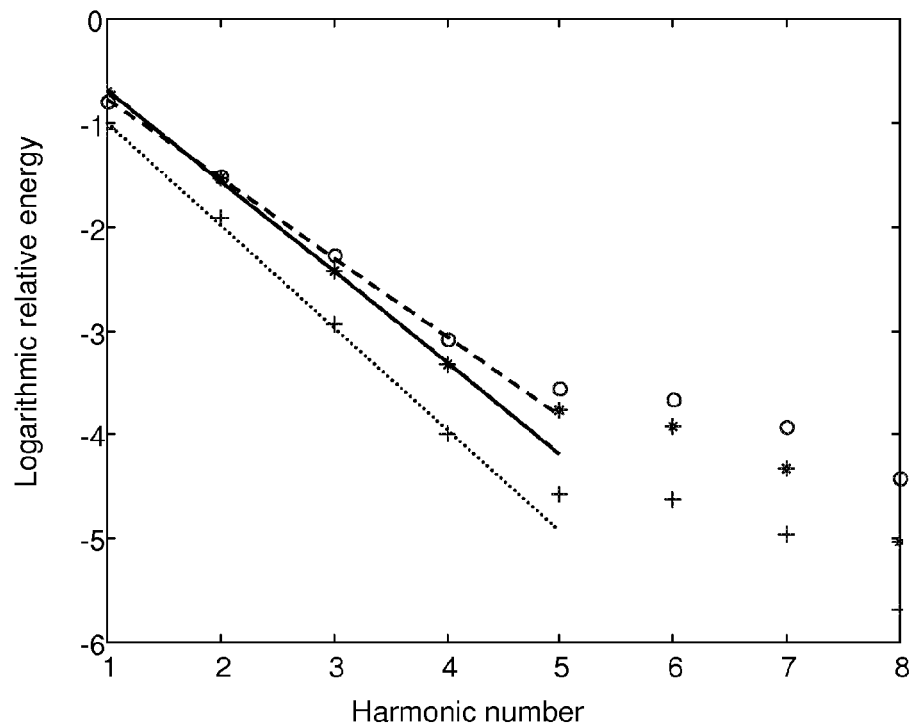
FIG. 16(b) represents corresponding frequency spectra for three different flow rates, wherein each frequency spectrum is given in logarithmic scale and mapped to harmonic numbers.
Figure 16C:
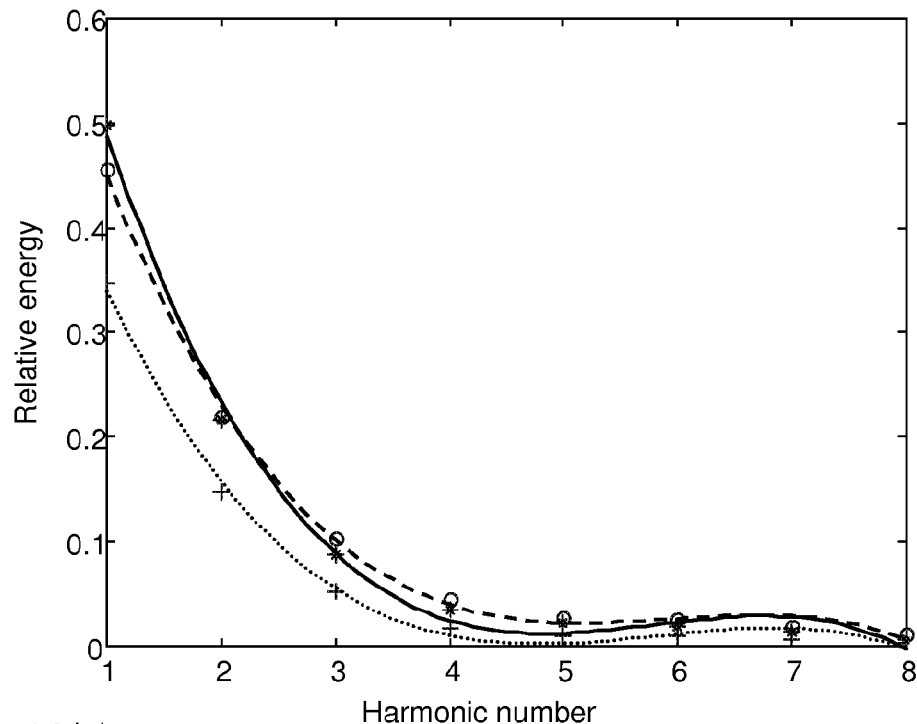
FIG. 16(c) is a plot of the data in FIG. 16(b) in linear scale.

FIG. 16(a) represents an energy spectrum of a reference signal acquired at a flow rate of 300 ml/min in the system of FIG. 1. In this example, the reference signal essentially consists of a basic pump frequency at 1.2 Hz ($f_0$, first harmonic) and a set of overtones of this frequency (second and further harmonics). Compared to the power spectrum of FIG. 2(b), the pressure signals used for generating the graphs in FIG. 16(a)-16(d) do not contain any significant frequency component at 0.5 $f_0$ and its harmonics. The graph in FIG. 16(a) displays the relative energy distribution, wherein the energy values have been normalized to the total energy for frequencies in the range of 0-10 Hz. FIG. 16(b) represents energy spectra of reference signals acquired at three different flow rates in the system of FIG. 1. The energy spectra are given in logarithmic scale versus harmonic number (first, second, etc). As shown, an approximate linear relationship may be identified between the logarithmic energy and harmonic number for the first four to five harmonic numbers. This indicates that each energy spectrum may be represented by a respective exponential/polynomial function. FIG. 16(c) illustrates the data of FIG. 16(b) in linear scale, wherein a respective polynomial function has been fitted to the data. As indicated in FIGS. 16(a)-16(c), the energy spectra may be represented in different formats in the reference library, e.g. as a set of energy values associated with discrete frequency values or harmonic numbers, or as an energy function representing energy versus frequency/harmonic number.

Figure 16D:
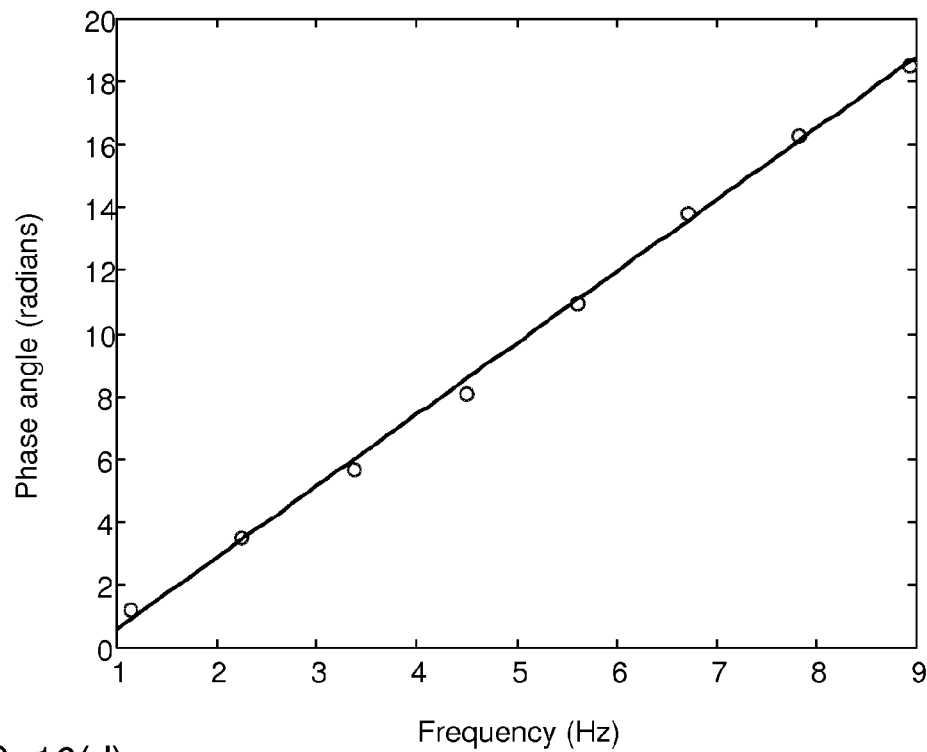
FIG. 16(d) is a phase angle spectrum corresponding to the frequency spectrum in FIG. 16(a).

FIG. 16(d) illustrates a phase angle spectrum acquired together with the energy spectrum in FIG. 16(a), i.e. for a flow rate of 300 ml/min The graph in FIG. 16(d) illustrates phase angle as a function of frequency, and a linear function has been fitted to the data. In an alternative representation (not shown), the phase spectrum may be given as a function of harmonic number. Like the energy spectra, the phase spectra may be represented in different formats in the reference library, e.g. as a set of phase angle values associated with discrete frequency values or harmonic numbers, or as a phase function representing phase angle versus frequency/harmonic number.

From the above, it should be understood that the energy and phase data that are stored the reference library may be used to generate a temporal reference profile. Each energy value in the energy data corresponds to an amplitude of a sinusoid with a given frequency (the frequency associated with the energy value), wherein the phase value for the given frequency indicates the proper phase angle of the sinusoid. This method of preparing the predicted temporal reference profile by combining (typically adding) sinusoids of appropriate frequency, amplitude and phase angle allows the predicted temporal reference profile to include all harmonics of the pump frequency within a desired frequency range.

When a reference profile (temporal or spectral) is to be generated, the reference library is first searched based on a current value of one or more system parameters, such as the current pump frequency. If no exact match is found in the reference library, a combination process may be executed to generate the reference profile. For example, the two closest matching pump frequencies may be identified in the reference library and the associated energy and phase data may be retrieved and combined to generate the reference profile. The combination may be done by interpolating the energy data and the phase data, respectively. In the example of FIGS. 16(a)-16(d), an interpolated energy value may be calculated for each harmonic number, and similarly an interpolated phase value may be calculated for each harmonic number. Any type of interpolation function may be used, be it linear or non-linear.

In the first, second and third embodiments, one and the same pressure sensor is suitably used in both the reference measurement and the actual monitoring process. Alternatively, different pressure sensor units may be used, provided that the pressure sensor units yield identical signal responses with respect to the pump pulses or that the signal responses may be matched using a known mathematical relationship.

To further improve the first, second and third embodiments, the process of generating the predicted reference profile (temporal or spectral) may also involve compensating for other potentially relevant factors that differ between the reference measurement and the current operational state. These so-called confounding factors may comprise one or more of the system parameters listed above, such as absolute average venous and arterial pressures, temperature, blood hematocrit/viscosity, gas volumes, etc. This compensation may be done with the use of predefined compensation formulas or look-up tables.

In further variations, the second and third embodiments may be combined, e.g. in that the reference library stores not only energy and phase data, but also temporal library profiles, in association with system parameter value(s). When an exact match is found in the library, the temporal library profile is retrieved from the library and used as the predicted reference profile, otherwise the predicted reference profile is obtained by retrieving and combining (e.g. interpolating) the energy and phase data, as in the third embodiment. In a variant, the predicted reference profile u(n) at the current pump frequency v is obtained by:

$$u(n)=r_i(n)-r'_i(n)+r'(n),$$

wherein $r_i(n)$ denotes a temporal library profile that is associated with the closest matching pump frequency $v_i$ in the reference library, $r'_i(n)$ denotes a temporal reference profile that is reconstructed from the energy and phase data associated with the closest matching pump frequency $v_i$ in the reference library, and $r'(n)$ denotes an estimated temporal reference profile at the current pump frequency v. The estimated temporal reference profile $r'(n)$ may be obtained by applying predetermined functions to estimate the energy and phase data, respectively, at the current pump frequency v based on the energy and phase data associated with the closest matching pump frequency $v_i$. With reference to FIGS. 16(b)-16(c), such a predetermined function may thus represent the change in energy data between different flow rates. Alternatively, the estimated temporal reference profile $r'(n)$ may be obtained by retrieving and combining (e.g. interpolating) energy and phase data for the two closest matching pump frequencies $v_i$ and $v_j$ as in the third embodiment.

As an alternative to the use of reference measurements, the reference profile may be obtained directly through simulations, i.e. calculations using a mathematical model of the extracorporeal circuit 20, based on current state information indicating the current operational state of the system. Such current state information may include a current value of one or more of the above-mentioned system parameters. The model may be based on known physical relationships of the system components (or via an equivalent representation, e.g. by representing the system as an electrical circuit with fluid flow and pressure being given by electrical current and voltage, respectively). The model may be expressed, implicitly or explicitly, in analytical terms. Alternatively, a numerical model may be used. The model may be anything from a complete physical description of the system to a simple function. In one example, such a simple function may convert data on the instantaneous angular velocity of the pump rotor 3' to a reference profile, using empirical or theoretical data. Such data on the instantaneous angular velocity might be obtained from the pump sensor 26 in FIG. 1.

In another embodiment, simulations are used to generate reference profiles for different operational states of the system. These reference profiles may then be stored in a reference library, which may be accessed and used in the same way as described above for the second and third embodiments. It is also to be understood that reference profiles (and/or corresponding energy and phase angle data) obtained by simulations may be stored together with reference profiles (and/or corresponding energy and phase angle data) obtained by reference measurement.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

For example, the integrity of the connection system may be decided based on a combination of different parameter values, which may be extracted from the monitoring signal according to any of the above-described examples.

Although certain pulse features have been described as being identified in the time domain, it may be equally possible to generate a frequency domain representation of the monitoring signal/evaluation segment and to identify, in the frequency domain representation, a pulse feature of one or more apparent pulses. The frequency domain representation may be generated by subjecting the monitoring signal/ evaluation segment to a frequency analysis, e.g. by Fourier analysis or an equivalent technique. The parameter value may, e.g., be calculated to represent relevant parts of the resulting energy spectrum and/or or phase angle spectrum Still further, the extracorporeal circuit may include any type of pumping device, not only rotary peristaltic pumps as disclosed above, but also other types of positive displacement pumps, such as linear peristaltic pumps, diaphragm pumps, as well as centrifugal pumps Embodiments of the invention are also applicable when the connection system comprises a single access device, such as in so-called single needle treatment.

The inventive technique is applicable to all types of extracorporeal blood flow circuits in which blood is taken from the systemic blood circuit of the patient to have a process applied to it before it is returned to the patient. Such blood flow circuits include circuits for hemodialysis, hemofiltration, hemodiafiltration, plasmapheresis, apheresis, extracorporeal membrane oxygenation, assisted blood circulation, extracorporeal liver support/dialysis, and blood fraction separation (e.g. cells) of donor blood. The inventive technique is likewise applicable for monitoring in other types of extracorporeal blood flow circuits, such as circuits for blood transfusion, infusion, as well as heart-lung-machines.

In a variation of the embodiments disclosed herein, the physiological pulses are supplemented by pressure pulses originating from a separate pulse generator which is attached to the patient to generate pressure waves in the vascular system of the patient. Such a pulse generator may be an ultrasound generator, a mechanical vibrator, a pressurized cuff, etc. Generally, the composite signal may be seen as comprising pump pulses and "patient pulses", which may be composed of physiological pulses and/or pulses from a separate pulse generator attached to the patient.

All of the above-described embodiments are based on analysing a composite signal for detection of a the disturbance caused by the superposition of patient pulses on pump pulses. However, it is not unlikely that all of the above-described embodiments are equally applicable to detect a disturbance in the pump profiles even if the patient pulses are too weak to emerge as such a disturbance. The present Assignee has surprisingly found that a disruption of the connection system C (FIG. 1) may be reflected in the shape of the pump pulses. This surprising effect is currently believed to be caused by the fact that the shape of the pump pulses depends on pressure variations within the blood vessel access itself. The pressure variations in the blood vessel access are influenced by pressure waves that propagate into the access via the venous and the arterial access devices 1, 14, i.e. pressure waves originating from the blood pump 3, and possibly other mechanical pulse generators in the extracorporeal circuit 20. The pressure waves in the blood vessel access will in turn propagate back into the extracorporeal circuit 20 and be detected by at least one of the pressure sensors 4a-4c. A disruption of the connection system C is likely to affect the pressure variations in the blood vessel access, and thus show up as a change or deformation of the pump pulses as detected by one of the pressure sensors 4a-4c in the extracorporeal circuit 20. The deformation (estimated by any of the above-mentioned pulse features) may vary between apparent pulses in the monitoring signal, since the conditions in the blood vessel access (e.g. with respect to local pressure, flow, etc) may vary when the pressure waves interact with blood vessel access. Furthermore, it is likely that the mechanical structure of the extracorporeal circuit 20 differs between an intact and a disrupted connection system C. For example, swinging movements and vibrations of tube segment(s) energized by the pumping actions of the blood pump may depend on the state of the connection system C. Any such changes in mechanical structure may emerge as a change in the shape/ magnitude/timing of the apparent pulses in the monitoring signal.

The above-described embodiments may also be applicable to monitoring of fault conditions in fluid containing systems containing other liquids than blood. Likewise, the connection system need not be provided in relation to a human or animal subject, but may be provided in relation to any other type of fluid containing system.

In one example, the connection system is provided between a blood processing circuit and a container/machine, wherein blood is pumped from one container/machine through a blood processing device in the blood processing circuit and back to the container/machine, or to another container/machine downstream of the blood processing device. The blood processing device may be any known device configured to modify and/or analyse the blood.

In a further example, the connection system is provided between a dialyser and a reprocessing system, which reprocesses the dialyser by pumping water, optionally together with suitable chemicals through the dialyser. An example of a dialyser reprocessing system is known from US2005/ 0051472.

In another example, the connection system is provided between a dialysate supply and a dialysate regeneration system, which circulates dialysate from the dialysate supply through a dialysate regeneration device and back to the supply. An example of a dialysate regeneration device is known from WO 05/062973.

In yet another example, the connection system is provided in an arrangement for priming an extracorporeal blood flow circuit by pumping a priming fluid from a supply via the blood flow circuit to a dialyser. The priming fluid may e.g. be dialysis solution, saline, purified water, etc.

In a still further example, the connection system is provided in an arrangement for cleaning and disinfecting the dialysis solution flow path of a dialysis machine, which pumps a cleaning fluid via a flow path to a dialyser/dialyser tubing. The cleaning fluid may e.g. be hot water, a chemical solution, etc.

In a further example, the connection system is provided in an arrangement for purifying water, which pumps water from a supply through a purifying device. The purifying device may use any known water purification technique, e.g. reverse osmosis, deionization or carbon absorption.

In another example, the connection system is provided in an arrangement for providing purified water to a dialysis machine, e.g. to be used in the preparation of dialysis solution therein.

In all of these examples, and in other applications related to medical treatment of human or animal patients, it may be vital to monitor the integrity of the connection system and/or the operation of pumping devices. Such monitoring may be accomplished according to the embodiments disclosed herein.

The above-described monitoring process may executed by a surveillance device (cf. 25 in FIG. 1), which may be implemented by special-purpose software (or firmware) run on one or more general-purpose or special-purpose computing devices. In this context, it is to be understood that each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software controlled computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The surveillance device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software, and the adjustment factors, may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The surveillance device may include one or more communication interfaces, such as a serial interface, a parallel interface, a USB interface, a wireless interface, a network adapter, etc, as well as one or more data acquisition devices, such as an A/D converter. The special-purpose software may be provided to the surveillance device on any suitable computer-readable medium, including a record medium, a read-only memory, or an electrical carrier signal.

It is also conceivable that some (or all) method steps are fully or partially implemented by dedicated hardware, such as an FPGA, an ASIC, or an assembly of discrete electronic components (resistors, capacitors, operational amplifier, transistors, filters, etc), as is well-known in the art.

In the following, a set of items are recited to summarize some aspects and embodiments of the invention as disclosed in the foregoing.

Item 1. A method for monitoring the integrity of a connection system (C) between first and second fluid containing systems, wherein the first fluid containing system (20) comprises a first pulse generator (3), and the second fluid containing system comprises a second pulse generator, and wherein at least one pressure sensor (4a-4c) is arranged in the first fluid containing system (20) to detect first pulses originating from the first pulse generator (3) and second pulses originating from the second pulse generator, said method comprising:

generating a time-dependent monitoring signal based on measurement data obtained from said at least one pressure sensor (4a-4c) such that the monitoring signal contains a sequence of apparent pulses, said apparent pulses representing a superposition of the second pulses on the first pulses when the connection system (C) is intact;

processing the monitoring signal to calculate a parameter value based on a pulse feature of at least one of the apparent pulses in the monitoring signal, parameter value representing a disturbance caused by the superposition of the second pulses on the first pulses; and determining the integrity of the connection system (C) based at least partly on the parameter value. The monitoring signal may be processed in the time domain to identify the pulse feature of the apparent puls(es), whereby the pulse feature is a temporal characteristic of the apparent pulse.

Item 2. The method of item 1, wherein each pulse feature is indicative of at least one of a magnitude, a timing and a shape of one of the apparent pulses.

Item 3. The method of item 1 or 2, wherein the parameter value is calculated as a symmetry measure between at least two of the apparent pulses.

Item 4. The method of any one of items 1-3, wherein the step of processing further comprises: comparing at least one pair of pulse features obtained from a set of apparent pulses.

Item 5. The method of item 4, wherein the set of apparent pulses is selected to yield a known relation between said at least one pair of pulse features when the connection system (C) is compromised.

Item 6. The method of item 1 or 2, wherein the pulse feature comprises shape-indicative data and the step of calculating comprises: obtaining reference data, and comparing the shape-indicative data to the reference data.

Item 7. The method of item 6, wherein the shape-indicative data comprises signal values in the monitoring signal, and the reference data comprises a temporal reference profile.

Item 8. The method of item 7, wherein said comparing comprises: obtaining timing information indicative of the timing of the first pulses in the monitoring signal, and using the timing information to align the signal values in the monitoring signal with the temporal reference profile.

Item 9. The method of any one of items 6-8, wherein the parameter value is indicative of a similarity or a deviation between the shape-indicative data and the reference data.

Item 10. The method of any one of items 6-9, wherein the reference data is representative of the shape of at least one first pulse.

Item 11. The method of any one of items 6-10, wherein the shape-indicative data is extracted by an analysis of the frequency content of the monitoring signal, and wherein the reference data is at least representative of an amplitude spectrum Item 12. The method of item 11, wherein the shape-indicative data is further extracted by an analysis of the phase content of the monitoring signal, and wherein the reference data is further representative of a phase spectrum Item 13. The method of any one of items 6-12, further comprising the step of obtaining a current value of one or more system parameters of the first fluid containing system, and the step of obtaining the reference data as a function of the current value.

Item 14. The method of item 13, wherein said one or more system parameters is indicative of the rate of first pulses in the first fluid containing system (20).

Item 15. The method of any one of items 6-9, wherein the step of obtaining the reference data comprises: deriving, based on timing information indicative of the timing of the first pulses in the monitoring signal, a set of signal segments in the monitoring signal; and aligning and combining the signal segments, based on the timing information, to generate the reference data as an average signal profile.

Item 16. The method of any preceding item, wherein the step of processing further comprises: identifying each pulse feature based on timing information which is indicative of the timing of the first pulses in the monitoring signal.

Item 17. The method of any one of items 1-16, wherein the step of processing further comprises: identifying each pulse feature based on an identification of given signal features in the apparent pulses.

Item 18. The method of any preceding item, wherein the step of processing comprises: generating an envelope for a sequence of apparent pulses in the monitoring signal, and identifying said pulse feature in the envelope.

Item 19. The method of item 18, wherein the step of generating the envelope comprises: determining a magnitude value for each apparent pulse, and generating the envelope as a sequence of the magnitude values.

Item 20. The method of item 1 or 2, wherein the step of processing comprises: calculating the parameter value as a statistical dispersion measure of the pulse features of a plurality of apparent pulses.

Item 21. The method of item 1 or 2, wherein the step of processing comprises: generating a frequency domain representation of the monitoring signal, and calculating the parameter value based on the frequency domain representation.

Item 22. The method of any preceding item, wherein the step of determining the integrity comprises: calculating a statistical measure of a plurality of parameter values, and evaluating the statistical measure, each parameter value being calculated by processing a respective time segment in the monitoring signal.

Item 23. The method of item 1, wherein the step of processing comprises: calculating the parameter value as a statistical dispersion measure of signal values in the monitoring signal.

Item 24. The method of any preceding item, wherein the first fluid containing system is an extracorporeal blood processing system (20), wherein the second fluid containing system is a vascular system of a subject, and wherein the connection system (C) comprises an access device (1, 14) for connection to a blood vessel access of the vascular system.

Item 25. The method of item 23, wherein the second pulses originate from one or more physiological pulse generators in the subject.

Item 30. A computer program product comprising instructions for causing a computer to perform the method of any one of claims 1-25.

Item 40. A device for monitoring the integrity of a connection system (C) between first and second fluid containing systems, wherein the first fluid containing system (20) comprises a first pulse generator (3), and the second fluid containing system comprises a second pulse generator, and wherein at least one pressure sensor (4a-4c) is arranged in the first fluid containing system (20) to detect first pulses originating from the first pulse generator (3) and second pulses originating from the second pulse generator, said device comprising:

means (29) for generating a time-dependent monitoring signal based on measurement data obtained from said at least one pressure sensor (4a-4c) such that the monitoring signal contains a sequence of apparent pulses, said apparent pulses representing a superposition of the second pulses on the first pulses when the connection system (C) is intact;

means (29) for processing the monitoring signal to calculate a parameter value based on a pulse feature of at least one of the apparent pulses in the monitoring signal, the parameter value representing a disturbance caused by the superposition of the second pulses on the first pulses; and means (29) for determining the integrity of the connection system (C) based at least partly on the parameter value.

Item 41. A device for monitoring the integrity of a connection system (C) between first and second fluid containing systems, wherein the first fluid containing system (20) comprises a first pulse generator (3), and the second fluid containing system comprises a second pulse generator, and wherein at least one pressure sensor (4a-4c) is arranged in the first fluid containing system (20) to detect first pulses originating from the first pulse generator (3) and second pulses originating from the second pulse generator, said device comprising:

an input (28) for obtaining measurement data from said at least one pressure sensor (4a-4c), and a signal processor (29) connected to said input and being configured to generate a time-dependent monitoring signal based on the measurement data, such that the monitoring signal contains a sequence of apparent pulses, said apparent pulses representing a superposition of the second pulses on the first pulses when the connection system (C) is intact; to process the monitoring signal for calculation of a parameter value based on a pulse feature of at least one of the apparent pulses in the monitoring signal, the parameter value representing a disturbance caused by the superposition of the second pulses on the first pulses; and to determine the integrity of the connection system (C) based at least partly on the parameter value.

Embodiments of the device as set forth in item 40 or 41 may correspond to the embodiments of the method as set forth in items 2-25.

The invention claimed is:

1. A method comprising:
providing a connection system between a first fluid containing system and a second fluid containing system, a first pulse generator comprising a pump in the first fluid containing system configured to generate first pulses formed by a plurality of frequency components, and at least one pressure sensor in the first fluid containing system configured to detect the plurality of frequency components from the first pulse generator;

generating measurement data from the at least one pressure sensor configured to detect second pulses from a second pulse generator in the second fluid containing system when the connection system is intact;

generating a time-dependent monitoring signal based on the measurement data that retains multiple frequency components of the plurality of frequency components and contains a sequence of apparent pulses, said apparent pulses representing a superposition of the second pulses on the first pulses when the connection system is intact;

calculating a superposition disturbance parameter value based on a pulse feature representing at least one of a magnitude feature, a timing feature, and a shape feature of at least one of the apparent pulses in the monitoring signal retaining the multiple frequency components, the superposition disturbance parameter value representing a disturbance caused by the superposition of the second pulses on the first pulses when the connection system is intact;

determining the integrity of the connection system based at least partly on the calculated superposition disturbance parameter value; and performing, in response to determining that the integrity of the connection system has been compromised, at least one of: issuing an alarm to a user to take appropriate action, stopping the pump in the first fluid containing system, and activating a clamping device on the first fluid containing system.

2. The method of claim 1, wherein the parameter value is calculated as a symmetry measure between at least two of the apparent pulses.

3. The method of claim 1, wherein processing the monitoring signal further comprises comparing at least one pair of pulse features obtained from a set of apparent pulses.

4. The method of claim 3, wherein the set of apparent pulses is selected to yield a known relation between said at least one pair of pulse features when the connection system is compromised.

5. The method of claim 1, wherein the pulse feature comprises shape-indicative data and calculating the parameter value comprises: obtaining reference data, and comparing the shape-indicative data to the reference data.

6. The method of claim 5, wherein the shape-indicative data comprises signal values in the monitoring signal, and the reference data comprises a temporal reference profile.

7. The method of claim 6, wherein said comparing comprises: obtaining timing information indicative of the timing of the first pulses in the monitoring signal, and using the timing information to align the signal values in the monitoring signal with the temporal reference profile.

8. The method of claim 5, wherein the parameter value is indicative of a similarity or a deviation between the shape-indicative data and the reference data.

9. The method of claim 5, wherein the reference data is representative of the shape of at least one first pulse.

10. The method of claim 5, wherein the shape-indicative data is extracted by an analysis of the frequency content of the monitoring signal, and wherein the reference data is at least representative of an amplitude spectrum.

11. The method of claim 10, wherein the shape-indicative data is further extracted by an analysis of the phase content of the monitoring signal, and wherein the reference data is further representative of a phase spectrum.

12. The method of claim 5, further comprising obtaining a current value of one or more system parameters of the first fluid containing system, and obtaining the reference data as a function of the current value.

13. The method of claim 12, wherein said one or more system parameters is indicative of the rate of first pulses in the first fluid containing system.

14. The method of claim 5, wherein obtaining the reference data comprises: deriving, based on timing information indicative of the timing of the first pulses in the monitoring signal, a set of signal segments in the monitoring signal; and aligning and combining the signal segments, based on the timing information, to generate the reference data as an average signal profile.

15. The method of claim 1, wherein processing the monitoring signal further comprises identifying the pulse feature based on timing information which is indicative of the timing of the first pulses in the monitoring signal.

16. The method of claim 1, wherein processing the monitoring signal further comprises identifying the pulse feature based on an identification of given signal features in the apparent pulses.

17. The method of claim 1, wherein processing the monitoring signal comprises: generating an envelope for a sequence of apparent pulses in the monitoring signal, and identifying said pulse feature in the envelope.

18. The method of claim 17, wherein generating the envelope comprises: determining a magnitude value for each apparent pulse, and generating the envelope as a sequence of the magnitude values.

19. The method of claim 1, wherein processing the monitoring signal comprises calculating the parameter value as a statistical dispersion measure of the pulse feature of a plurality of apparent pulses.

20. The method of claim 1, wherein processing the monitoring signal comprises: generating a frequency domain representation of the monitoring signal, and calculating the parameter value based on the frequency domain representation.

21. The method of claim 1, wherein determining the integrity comprises:
calculating a statistical measure of a plurality of parameter values including the parameter value, wherein each of the plurality of parameter values is calculated by processing a respective time segment in the monitoring signal; and
evaluating the statistical measure to determine the integrity of the connection system at least partly in response to the statistical measure.

22. The method of claim 1, wherein processing the monitoring signal comprises: calculating the parameter value as a statistical dispersion measure of signal values in the monitoring signal.

23. The method of claim 1, wherein the first fluid containing system is an extracorporeal blood processing system, wherein the second fluid containing system is a vascular system of a subject, and wherein the connection system comprises an access device configured to connect to a blood vessel access of the vascular system.

24. The method of claim 1, wherein the second pulses originate from one or more physiological pulse generators in the subject.

25. The method of claim 1, wherein the plurality of frequency components comprises:

a base frequency component ($f_0$); and
at least one other frequency component spaced in frequency at least $0.5f_0$ from the base frequency component.

26. A computer readable medium comprising instructions which, when executed by a processor, cause the processor to monitor the integrity of a connection system between first and second fluid containing systems by:
receiving measurement data from at least one pressure sensor configured to detect first and second pulses when the connection system is intact, first pulses formed by a plurality of frequency components originating from a first pulse generator comprising a pump in the first fluid containing system, second pulses originating from a second pulse generator in the second fluid containing system;
generating a time-dependent monitoring signal based on the measurement data that retains multiple frequency components of the plurality of frequency components and contains a sequence of apparent pulses, said apparent pulses representing a superposition of the second pulses on the first pulses when the connection system is intact;
calculating a superposition disturbance parameter value based on a pulse feature representing at least one of a magnitude feature, a timing feature, and a shape feature of at least one of the apparent pulses in the monitoring signal retaining the multiple frequency components, the superposition disturbance parameter value representing a disturbance caused by the superposition of the second pulses on the first pulses when the connection system is intact;
determining the integrity of the connection system based at least partly on the calculated superposition disturbance parameter value; and
generating, in response to determining that the integrity of the connection system has been compromised, at least one of: an alarm signal for a user to take appropriate action, a pump stop signal to stop the pump in the first fluid containing system, and a clamping signal to activate a clamp device on the first fluid containing system.

27. A device comprising:
a connection system between a first fluid containing system and a second fluid containing system, a first pulse generator comprising a pump in the first fluid containing system configured to generate first pulses formed by a plurality of frequency components, and at least one pressure sensor in the first fluid containing system configured to detect the plurality of frequency components from the first pulse generator;
means for generating measurement data from the at least one pressure sensor configured to detect second pulses from a second pulse generator in the second fluid containing system when the connection system is intact;
means for generating a time-dependent monitoring signal based on the measurement data that retains multiple frequency components of the plurality of frequency components and contains a sequence of apparent pulses, said apparent pulses representing a superposition of the second pulses on the first pulses when the connection system is intact;
means for calculating a superposition disturbance parameter value based on a pulse feature representing at least one of a magnitude feature, a timing feature, and a shape feature of at least one of the apparent pulses in the monitoring signal retaining the multiple frequency components, the superposition disturbance parameter value representing a disturbance caused by the superposition of the second pulses on the first pulses when the connection system is intact;
means for determining the integrity of the connection system based at least partly on the calculated superposition disturbance parameter value; and
means for performing, in response to determining that the integrity of the connection system has been compromised, at least one of: issuing an alarm to a user to take appropriate action, stopping the pump in the first fluid containing system, and activating a clamping device on the first fluid containing system.

28. A device comprising:
a connection system between a first fluid containing system and a second fluid containing system, a first pulse generator comprising a pump in the first fluid containing system configured to generate first pulses formed by a plurality of frequency components, and at least one pressure sensor in the first fluid containing system configured to detect the plurality of frequency components from the first pulse generator;
an input configured to obtain measurement data from said at least one pressure sensor configured to detect second pulses from a second pulse generator in the second fluid containing system when the connection system is intact, and
a signal processor connected to said input and being configured to:
generate a time-dependent monitoring signal based on the measurement data, such that the monitoring signal retains multiple frequency components of the plurality of frequency components and contains a sequence of apparent pulses, said apparent pulses representing a superposition of the second pulses on the first pulses when the connection system is intact;
calculate a superposition disturbance parameter value based on a pulse feature representing at least one of a magnitude feature, a timing feature, and a shape feature of at least one of the apparent pulses in the monitoring signal retaining the multiple frequency components, the superposition disturbance parameter value representing a disturbance caused by the superposition of the second pulses on the first pulses when the connection system is intact;
determine the integrity of the connection system based at least partly on the calculated superposition disturbance parameter value; and
generate, in response to determining that the integrity of the connection system has been compromised, at least one of: an alarm signal for a user to take appropriate action, a pump stop signal to stop the pump in the first fluid containing system, and a clamping signal to activate a clamp device on the first fluid containing system.

* * * * *